United States Patent
Kim et al.

(10) Patent No.: US 12,357,838 B2
(45) Date of Patent: Jul. 15, 2025

(54) WEARABLE CARDIOVERTER DEFIBRILLATOR (WCD) SYSTEM SELECTING PREVIOUSLY IDENTIFIED PREFERRED CHANNEL FOR ATTEMPTING TO DETECT PACING ARTIFACTS

(71) Applicant: WEST AFFUM HOLDINGS DAC, Dublin (IE)

(72) Inventors: Jaeho Kim, Redmond, WA (US); Gregory T. Kavounas, Bellevue, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 497 days.

(21) Appl. No.: 17/490,296

(22) Filed: Sep. 30, 2021

(65) Prior Publication Data
US 2022/0105351 A1   Apr. 7, 2022

Related U.S. Application Data

(60) Provisional application No. 63/085,924, filed on Sep. 30, 2020.

(51) Int. Cl.
*A61N 1/04*     (2006.01)
*A61N 1/365*    (2006.01)
*A61N 1/39*     (2006.01)

(52) U.S. Cl.
CPC ........... *A61N 1/3904* (2017.08); *A61N 1/046* (2013.01); *A61N 1/365* (2013.01)

(58) Field of Classification Search
CPC .............................. A61N 1/046; A61N 1/3904
(Continued)

(56) References Cited

U.S. PATENT DOCUMENTS

| | | |
|---|---|---|
| 3,724,455 A | 4/1973 | Unger |
| 4,583,524 A | 4/1986 | Hutchins |

(Continued)

FOREIGN PATENT DOCUMENTS

| | | |
|---|---|---|
| EP | 3380189 B1 | 10/2018 |
| WO | 1998039061 A2 | 9/1998 |

(Continued)

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Nicole F Lavert
(74) *Attorney, Agent, or Firm* — POLSINELLI PC

(57) ABSTRACT

A wearable cardioverter defibrillator (WCD) system is adapted for use by an ambulatory patient who already has an implanted pacemaker. If implanted, such a pacemaker may occasionally be emitting, without the knowledge of the WCD system, pacing signals that may be adding pacing artifacts to the ECG signal. The WCD system may use multiple electrodes to sense ECG signals along multiple vectors that have channels. In embodiments, the WCD system identifies a preferred one of its available channels according to how easily the pacing artifacts are detected within its ECG signal. When the patient's parameters indicate that an alert criterion is met, the WCD system may attempt to read the ECG signal from the preferred channel first. This way the WCD system may be able to identify faster the pacing artifacts, and therefore analyze the ECG signal faster, with an opportunity to react faster to the alert criterion being met.

23 Claims, 18 Drawing Sheets

SAMPLE COMPONENTS OF WEARABLE CARDIOVERTER DEFIBRILLATOR (WCD) SYSTEM

(58) Field of Classification Search
USPC .......................................................... 607/2
See application file for complete search history.

(56) References Cited

U.S. PATENT DOCUMENTS

| | | | |
|---|---|---|---|
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Born et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,618,208 A | 4/1997 | Crouse et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 9,878,171 B2 | 1/2018 | Kaib |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |
| 2018/0093102 A1* | 4/2018 | Sullivan ............... A61N 1/3987 |

FOREIGN PATENT DOCUMENTS

WO        2012064604 A1    5/2012
WO    WO-2019144103 A1 *   7/2019 ......... A61B 18/1492

OTHER PUBLICATIONS

LIFECOR LifeVest System Model WCD 3100 Operator's Manual, 2006, Pn 20B0040 Rev FI, Zoll Lifecor Corporation, Pittsburgh, PA.
LifeVest Model 4000 Patient Manual, Zoll, 2009, PN 20B0047 Rev B.
Heartstart MRx and XL AED Algorithm—Application Note, Jul. 2001, Edition 2 Philips Healthcare, USA.
The LifeVest Network/Patient Data Management System, Zoll, 2015, 20C0503 Rev A.
Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.
Pagan-Carlo, et al., "Encircling Overlapping Multipulse Shock Waveforms for Transthoracic Defibrillation," JACC Journals, Dec. 1998, vol. 32 Issue 7, p. 2065-2071.
Low Power, Five Electrode Electrocardiogram (ECG) Analog Front End, Data Sheet ADAS1000/ADAS1000-1/ADAS1000-2, Analog Devices, 2012, Rev. B.
Sabbagh E, Abdelfattah T, Karim MM, Farah A, Grubb B, Karim S., Causes of Failure to Capture in Pacemakers and Implantable Cardioverter-defibrillators, J Innov Card Rhythm Manage, Feb. 15, 2020;11(2):4013-4017.

* cited by examiner

SAMPLE COMPONENTS OF WEARABLE CARDIOVERTER DEFIBRILLATOR (WCD) SYSTEM

SAMPLE COMPONENTS OF EXTERNAL DEFIBRILLATOR

COMPONENTS OF SAMPLE WCD SYSTEM

*STORING THE IDENTIFIED PREFERENTIAL CHANNEL MEMORY IMPLEMENTATION*

*STORING THE IDENTIFIED PREFERENTIAL CHANNEL INPUT MULTIPLEXER IMPLEMENTATION*

FIG. 8                                                    METHODS

FIG. 9  *METHODS*

FIG. 10  _IDENTIFYING PREFERENTIAL CHANNEL_

IDENTIFYING CANDIDATE PACED QRS COMPLEXES

AVERAGING IDENTIFIED CANDIDATE PACED QRS COMPLEXES

AVERAGING PACED QRS COMPLEXES

FIG. 15 METHODS

METHODS

EXTRACTING THE PACING RATE OF THE PACING SIGNALS FROM THE DETECTED PACING ARTIFACTS

FIG. 18  *METHODS*

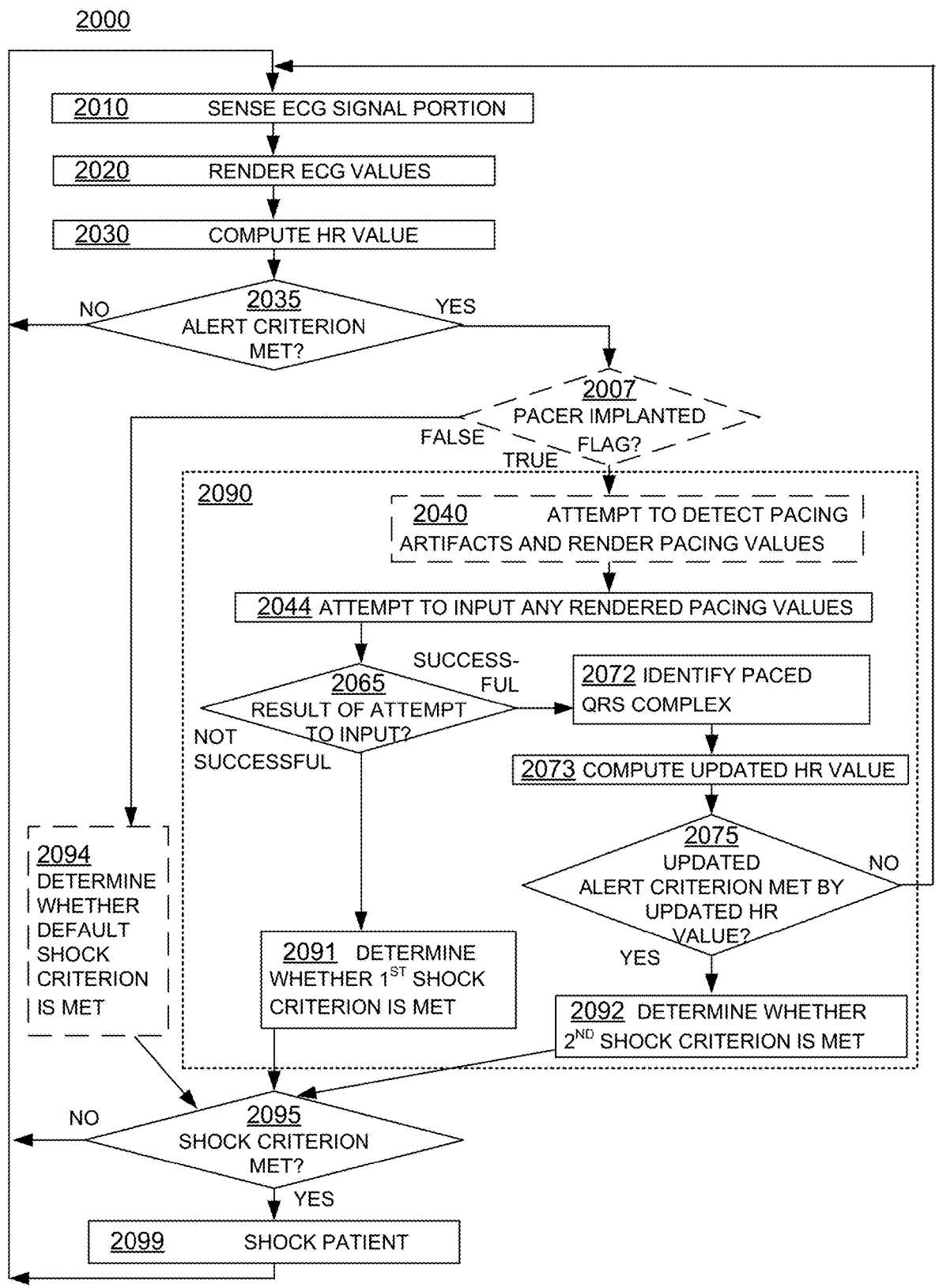
FIG. 20      METHODS

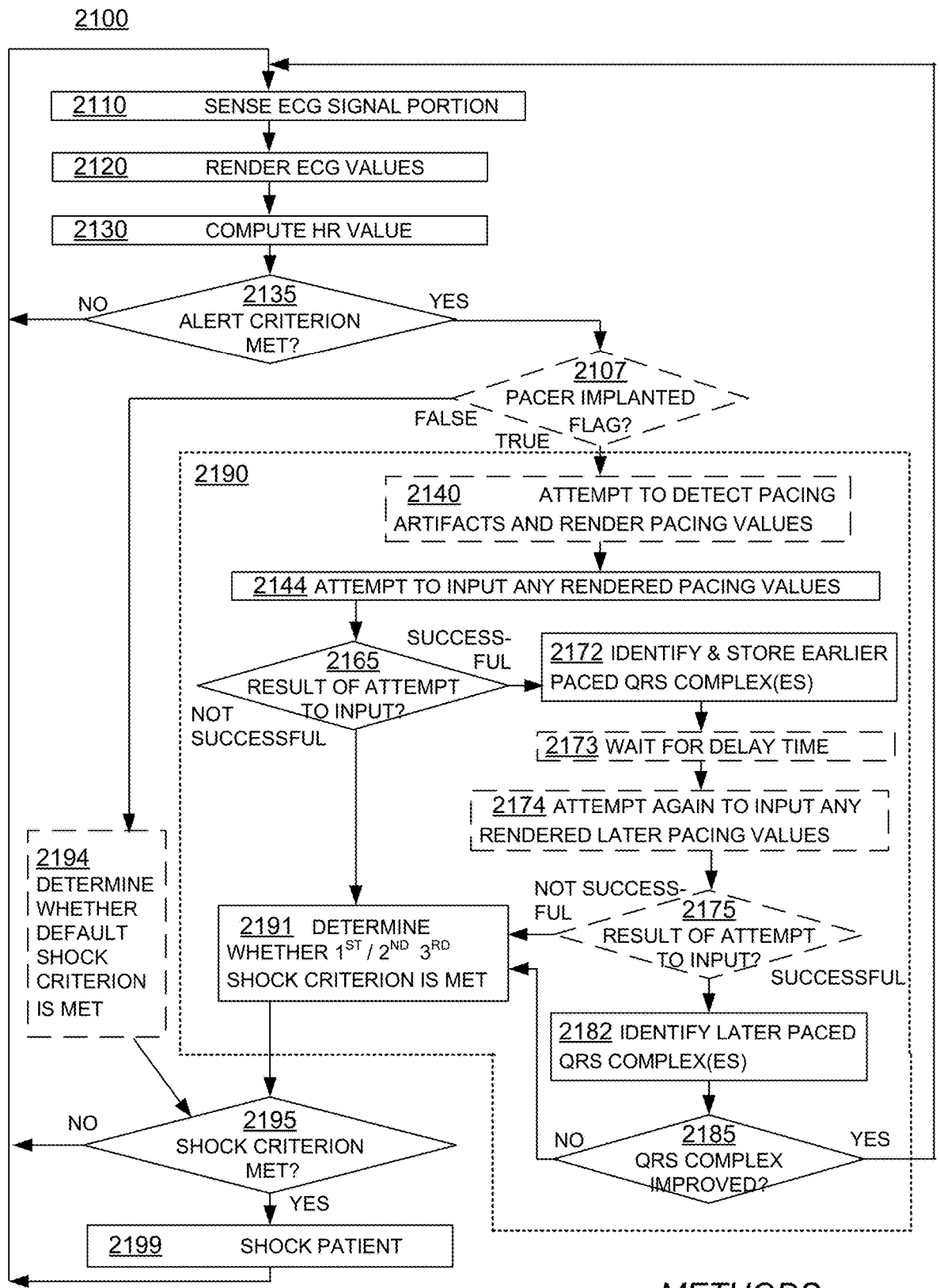
FIG. 21 METHODS

WEARABLE CARDIOVERTER DEFIBRILLATOR (WCD) SYSTEM SELECTING PREVIOUSLY IDENTIFIED PREFERRED CHANNEL FOR ATTEMPTING TO DETECT PACING ARTIFACTS

CROSS REFERENCE TO RELATED PATENT APPLICATIONS

This patent application claims priority from U.S. provisional patent application Ser. No. 63/085,924, filed on Sep. 30, 2020.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers may have thought that SCA is the same as a heart attack, but it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers one or more electric shocks through the heart. In some instances, these arrythmias are of the type that lead to SCA, and the electric shock delivered by the ICD is an internal defibrillation shock. (An internal defibrillation shock typically needs to be less strong than an external defibrillation shock.) In some instances, an ICD also includes a pacing function, in which case the ICD operates also as a pacemaker. For the pacing function, therefore, these arrythmias are of the type where the heart rate deviates from a normal range, for example by being lower than normal, a phenomenon that is called bradycardia. For pacing, the ICD delivers electric stimulations that are also called internal pacing signals. Pacing signals, which are also known as pacing pulses, are typically much weaker than defibrillation shocks.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart, and thus save their life.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventor(s). This approach in and of itself may also be inventive.

BRIEF SUMMARY

The present description gives instances of wearable cardioverter defibrillator (WCD) systems, storage media that may store programs, and methods, the use of which may help overcome problems and limitations of the prior art.

In embodiments, a wearable cardioverter defibrillator (WCD) system is adapted for use by an ambulatory patient who may or may not already have an implanted pacemaker. If implanted, such a pacemaker may occasionally be emitting, without the knowledge of the WCD system, pacing signals that may be adding pacing artifacts to the ECG signal. The WCD system may use multiple electrodes to sense ECG signals along multiple vectors. In embodiments, the WCD system identifies a preferred one of its available channels according to how easily the pacing artifacts are detected within its ECG signal. When the patient's parameters indicate that an alert criterion is met, the WCD system may attempt to read the ECG signal from the preferred channel first. An advantage can be that the WCD system may be able to identify faster the pacing artifacts, and therefore analyze the ECG signal faster, with an opportunity to react faster to the alert criterion being met.

In embodiments, a wearable cardioverter defibrillator (WCD) system is adapted for use by an ambulatory patient who may or may not already have an implanted pacemaker. If implanted, such a pacemaker may occasionally be emitting, without the knowledge of the WCD system, pacing signals that may be adding pacing artifacts to the ECG signal. The WCD system may identify these pacing artifacts and, from these it may infer when the pacing signals were emitted. The WCD system may further identify the resulting, induced paced QRS complexes, which may be different from the patient's ordinary QRS complexes. In embodiments, the WCD system uses a previously identified and stored baseline paced QRS complex for severity determination of a patient event. An advantage can be that paced QRS complexes might not be confused for noise in certain circumstances, thereby improving the performance of the system.

In embodiments, a wearable cardioverter defibrillator (WCD) system is adapted for use by an ambulatory patient who may or may not already have an implanted pacemaker. If implanted, such a pacemaker may occasionally be emitting, without the knowledge of the WCD system, pacing signals that may be adding pacing artifacts to the ECG signal. The WCD system may identify these pacing artifacts and therefore infer when the pacing signals were emitted. The WCD system may then decide if the detected pacing signals meet a regularity criterion, and it may even override an internal alert that is based on an elevated heart rate based on the pacing signals being regular. An advantage can be that the internal alert may be overridden internally, without alarming or even alerting the patient to sit still for a better ECG reading and analysis, asking them to confirm that they are alive, and so on.

In embodiments, a wearable cardioverter defibrillator (WCD) system is adapted for use by an ambulatory patient who may or may not already have an implanted pacemaker. If implanted, such a pacemaker may occasionally be emitting, without the knowledge of the WCD system, pacing signals that may be adding pacing artifacts to the ECG signal. The WCD system may identify these pacing artifacts and therefore detect paced QRS complexes, and then decide whether or not an updated alert criterion is met from the paced QRS complexes. If not, the WCD system may even override an earlier internal alert that could have been due to noise. An advantage can be that the earlier internal alert may be overridden internally, without alarming or even alerting the patient to sit still for a better ECG reading and analysis, asking them to confirm that they are alive, and so on.

In embodiments, a wearable cardioverter defibrillator (WCD) system is adapted for use by an ambulatory patient who may or may not already have an implanted pacemaker. If implanted, such a pacemaker may occasionally be emitting, without the knowledge of the WCD system, pacing signals that may be adding pacing artifacts to the ECG signal. The WCD system may identify these pacing artifacts and, from these detect, during a time of a patient crisis, an early paced QRS complex and a later paced QRS complex. The WCD system may then decide whether these meet an improvement criterion. If so, the WCD system may even override an earlier internal alert that could have been due to noise. The earlier internal alert may be overridden internally, without alarming or even alerting the patient to sit still for a better ECG reading and analysis, asking them to confirm that they are alive, etc.

These and other features and advantages of the claimed invention will become more readily apparent in view of the embodiments described and illustrated in this specification, namely in this written specification and the associated drawings.

BRIEF DESCRIPTION OF THE DRAWINGS

FIG. 20 is a flowchart for illustrating sample methods according to embodiments.

FIG. 21 is a flowchart for illustrating sample methods according to embodiments.

DETAILED DESCRIPTION

As has been mentioned, the present description is about wearable cardioverter defibrillator (WCD) systems, storage media that may store programs, and methods. Embodiments are now described in more detail.

A wearable cardioverter defibrillator (WCD) system according to embodiments may protect an ambulatory patient by electrically restarting their heart if needed. Such a WCD system may have a number of components. These components can be provided separately as modules that can be interconnected, or can be combined with other components, and so on.

Figure 1:
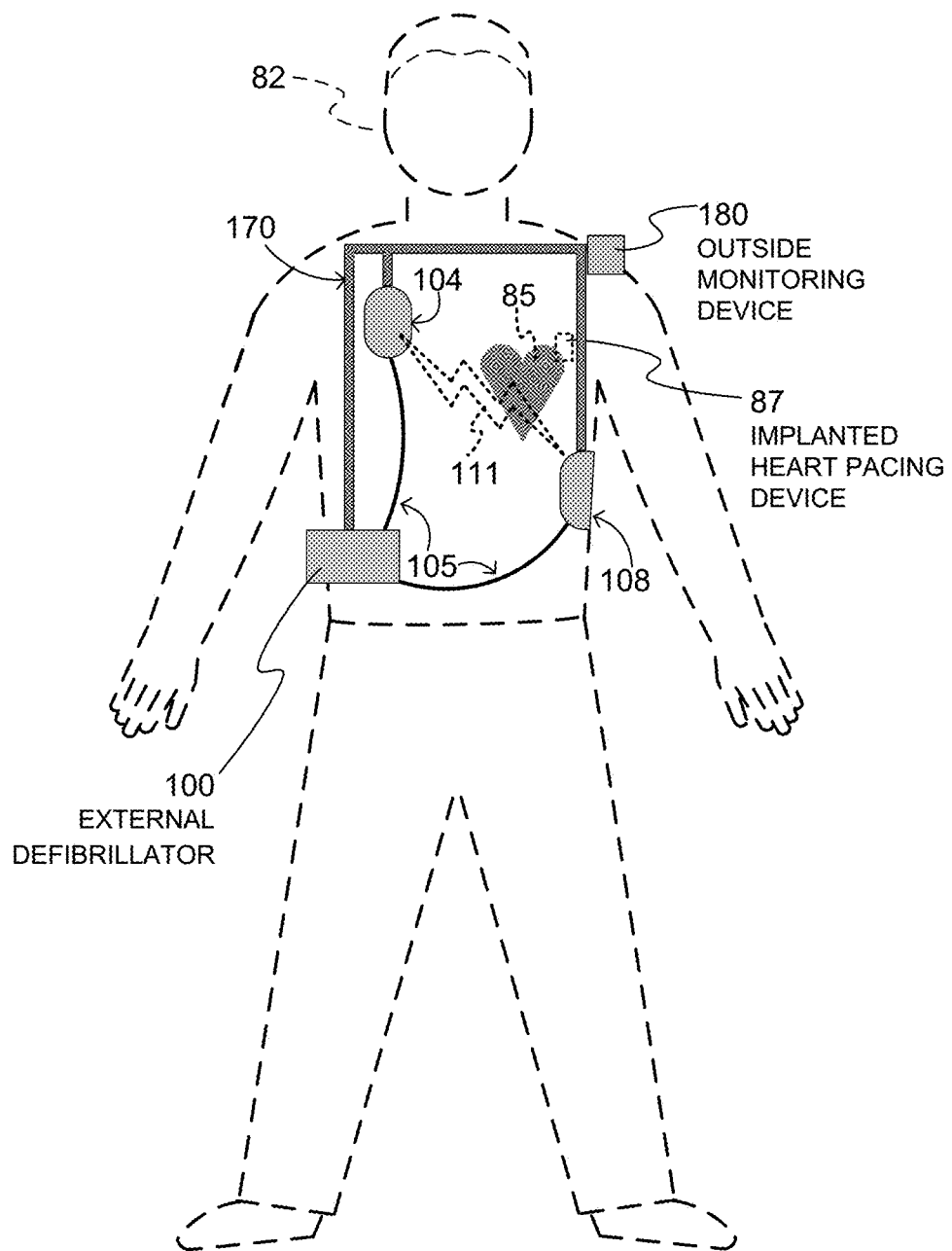
FIG. 1 is a diagram of sample components of a wearable cardioverter defibrillator (WCD) system that is configured for use by an ambulatory patient who has an implanted heart pacing device, the sample components made according to embodiments.

FIG. 1 depicts a patient 82. The patient 82 may also be referred to as the person 82 and/or wearer 82, since the patient 82 is wearing components of the WCD system. The patient 82 is ambulatory, which means that, while wearing the wearable portion of the WCD system, The patient 82 can walk around and is not necessarily bed-ridden. While the patient 82 may be considered to be also a "user" of the WCD system, this definition is not exclusive to the patient 82. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

The patient 82 may optionally have an implanted heart pacing device 87. Such a heart pacing device 87 is also called a pacemaker, a cardiac pacing device, a cardiac pacemaker, and so on. The heart pacing device 87 is a small device that is implanted into the patient 82 by surgery, and is used to replace and/or regulate the heartbeat of the patient 82. As such, the heart pacing device 87 can be active always, or only when it senses that the heart 85 is beating at an undesirable rate.

The heart pacing device 87 regulates the heartbeat by generating electrical impulses for the heart 85. These electrical impulses are also known as pacing signals. Technically speaking, these electrical impulses are delivered from the device 87 to the heart 85 by pacing electrodes. In practice, only one pacing electrode (not shown) is provided, while the heart pacing device 87 has an electrically conductive casing (often metallic) that serves as the second pacing electrode. In some cases, therefore, the heart pacing device 87 emits pacing signals only occasionally.

When delivered to the heart 85, each of these electrical impulses is intended to cause the heart muscle chambers to contract accordingly, and therefore pump blood. This heart contraction does not happen always, however. When that contraction actually happens, it is said that capture has been achieved. When that does not happen, and the phenomenon is called noncapture or loss of capture. In the event of noncapture, the implanted heart pacing device 87 is simply not having its desired effect.

The heart pacing device 87 is an example of an implanted device that does not include a defibrillation function. For instance, it is not part of an ICD. As such, the heart pacing device 87 is not capable of protecting the patient 82 from the above-mentioned risk of Sudden Cardiac Arrest (SCA). In fact, in some instances the patient 82 may be wearing a WCD system according to embodiments while waiting for surgery to receive an ICD in addition to or instead of the heart pacing device 87.

A such, a WCD system according to embodiments can be configured for use by the ambulatory patient 82, who has the implanted heart pacing device 87 that is configured to occasionally emit pacing signals. In particular, a WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

FIG. 1 depicts components of a WCD system made according to embodiments, which are worn by the patient 82. One such component is a support structure 170 that is wearable by the ambulatory patient 82. Accordingly, the support structure 170 can be configured to be worn by the ambulatory patient 82 for at least several hours per day, and also during the night. That, for at least several days, even a few months. It will be understood that the support structure 170 is shown only generically in FIG. 1, and in fact partly conceptually. FIG. 1 is provided merely to illustrate concepts about the support structure 170, and is not to be construed as limiting how the support structure 170 is implemented, or how it is worn.

The support structure 170 can be implemented in many different ways. For example, it can be implemented in a single component or a combination of multiple components. In embodiments, the support structure 170 could include a vest, a half-vest, a garment, etc. In such embodiments such items can be worn similarly to analogous articles of clothing. In embodiments, the support structure 170 could include a harness, one or more belts or straps, etc. In such embodiments, such items can be worn by the patient around the torso, hips, over the shoulder, etc. In embodiments, the support structure 170 can include a container or housing, which can even be waterproof. In such embodiments, the support structure can be worn by being attached to the patient's body by adhesive material, for example as shown and described in U.S. Pat. No. 8,024,037. The support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of the external defibrillator 100 include a housing and an energy storage module within the housing. As such, in the context of a WCD system, the defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient. This action is also called shocking the patient.

FIG. 1 also shows sample defibrillation electrodes 104, 108, which are coupled to external defibrillator 100 via electrode leads 105. The defibrillation electrodes 104, 108 can be configured to be worn by the patient 82 in a number of ways. For instance, the defibrillator 100 and the defibrillation electrodes 104, 108 can be coupled to the support structure 170, directly or indirectly. In other words, the support structure 170 can be configured to be worn by the ambulatory patient 82 so as to maintain at least one of the electrodes 104, 108 on the body of the ambulatory patient 82, while the patient 82 is moving around, etc. The electrode can be thus maintained on the body by being attached to the skin of the patient 82, simply pressed against the skin directly or through garments, etc. In some embodiments the electrode is not necessarily pressed against the skin, but becomes biased that way upon sensing a condition that could merit intervention by the WCD system. In addition, many of the components of the defibrillator 100 can be considered coupled to the support structure 170 directly, or indirectly via at least one of the defibrillation electrodes 104, 108.

When the defibrillation electrodes 104, 108 make good electrical contact with the body of the patient 82, the defibrillator 100 can administer, via the electrodes 104, 108, a brief, strong electric pulse 111 through the body. The pulse 111 is also known as shock, defibrillation shock, therapy, electrotherapy, therapy shock, etc. The pulse 111 is intended to go through and restart the heart 85, in an effort to save the life of the patient 82. Of course, the pulse 111 has a waveform suitable for this purpose. The pulse 111 can further include one or more pacing signals, also known as pacing pulses, of lesser magnitude to simply pace the heart 85 if needed, and so on.

A prior art defibrillator typically decides whether to defibrillate or not based on an ECG signal of the patient. However, the external defibrillator 100 may initiate defibrillation, or hold-off defibrillation, based on a variety of inputs, with the ECG signal merely being one of these inputs.

A WCD system according to embodiments can obtain data from the patient 82. For collecting such data, the WCD system may optionally include at least an outside monitoring device 180. The device 180 is called an "outside" device because it could be provided as a standalone device, for example not within the housing of the defibrillator 100. The device 180 can be configured to sense or monitor at least one local parameter. A local parameter can be a parameter of the patient 82, or a parameter of the WCD system, or a parameter of the environment, as will be described later in this document.

For some of these parameters, the device 180 may include one or more sensors or transducers. Each one of such sensors can be configured to sense a parameter of the patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about the patient 82 are also called physiological inputs and patient inputs. In embodiments, a sensor can be construed more broadly, as encompassing more than one individual sensors.

Optionally, the device 180 is physically coupled to the support structure 170. In addition, the device 180 may be communicatively coupled with other components that are coupled to the support structure 170. Such communication can be implemented by a communication module, as will be deemed applicable by a person skilled in the art in view of this description.

In embodiments, one or more of the components of the shown WCD system may be customized for the patient 82. This customization may include a number of aspects. For instance, the support structure 170 can be fitted to the body of the patient 82. For another instance, baseline physiological parameters of the patient 82 can be measured for various scenarios, such as when the patient is lying down (various orientations), sitting, standing, walking, running, and so on. These baseline physiological parameters can be the heart rate of the patient 82, motion detector outputs, one for each scenario, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data. Such other data may include whether it is known that the patient already has the implanted heart pacing device 87, what make and model it is, how it communicates outward, and so on. In some instances, the implanted heart pacing device 87 may communicate outward what it does for reception by a WCD system, and even when it does it, and the WCD system may adjust its operations accordingly, according to embodiments.

Figure 2:
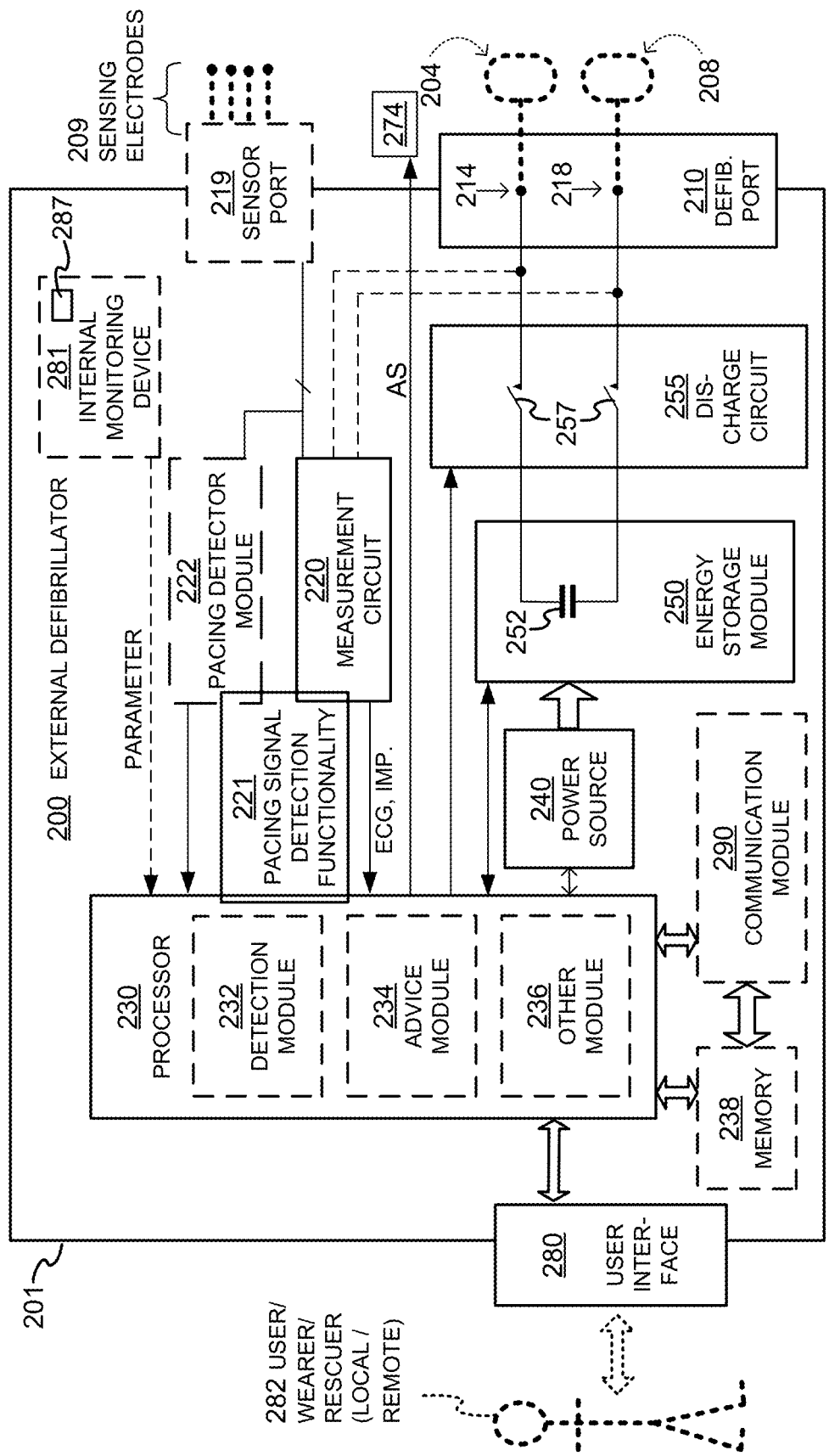
FIG. 2 is a diagram showing sample components of an external defibrillator, such as the one of the WCD system of FIG. 1, and which is made according to embodiments.

FIG. 2 is a diagram showing components of an external defibrillator 200, made according to embodiments. These components can be, for example, included in the external defibrillator 100 of FIG. 1. External defibrillator 200 is intended for a patient who would be carrying it on their body, such as by wearing it as shown for the ambulatory patient 82 of FIG. 1. The components shown in FIG. 2 can be provided in a housing 201, which may also be referred to as casing 201.

The defibrillator 200 may include a user interface (UI) 280 for a user 282. The user 282 can be the patient 82, also known as patient 282, also known as the wearer 282. Or, the user 282 can be a local rescuer at the scene, such as a bystander who might offer assistance, or a trained person. Or, the user 282 might be a remotely located trained caregiver in communication with the WCD system.

The user interface 280 can be made in a number of ways. The user interface 280 may include output devices, which can be visual, audible or tactile, for communicating to a user by outputting images, sounds or vibrations. Images, sounds, vibrations, and anything that can be perceived by the user 282 can also be called human-perceptible indications. As such, an output device according to embodiments can be configured to output a human-perceptible indication (HPI). Such HPIs can be used to alert the patient, sound alarms that may be intended also for bystanders, and so on. There are many examples of output devices. For example, an output device can be a light that can be turned on and off, a screen to display what is sensed, detected and/or measured, and provide visual feedback to the local rescuer 282 for their resuscitation attempts, and so on. Another output device can be a speaker, which can be configured to issue voice prompts, beeps, loud alarm sounds and/or words, and so on.

The user interface 280 may further include input devices for receiving inputs from users. Such users can be the patient 82, perhaps a local trained caregiver or a bystander, and so on. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

The defibrillator 200 may include an internal monitoring device 281. The device 281 is called an "internal" device because it is incorporated within the housing 201. The monitoring device 281 can sense or monitor patient parameters such as patient physiological parameters, system parameters and/or environmental parameters, all of which can be called patient data. In other words, the internal monitoring device 281 can be complementary or an alternative to the outside monitoring device 180 of FIG. 1. Allocating which of the parameters are to be monitored by which of the monitoring devices 180, 281 can be done according to design considerations. The device 281 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, the monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of the patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of the patient 282 will know about a condition that is either not improving or deteriorating.

Patient state parameters include recorded aspects of the patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within the outside monitoring device 180 or within the internal monitoring device 281. A motion detector of a WCD system according to embodiments can be configured to detect a motion event. A motion event can be defined as is convenient, for example a change in motion from a baseline motion or rest, etc. In such cases, a sensed patient parameter is motion. Such a motion detector can be made in many ways as is known in the art, for example by using an accelerometer and so on. In this example, a motion detector 287 is implemented within the monitoring device 281.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if the monitoring device 180 or 281 includes a GPS location sensor as per the above, and if it is presumed or sensed that the patient is wearing the WCD system.

The defibrillator 200 typically includes a defibrillation port 210, which can be a socket in the housing 201, or other equivalent structure. The defibrillation port 210 includes electrical nodes 214, 218. Leads of the defibrillation electrodes 204, 208, such as the leads 105 of FIG. 1, can be plugged into the defibrillation port 210, so as to make electrical contact with the nodes 214, 218, respectively. It is also possible that the defibrillation electrodes 204, 208 are connected continuously to the defibrillation port 210, instead. Either way, the defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

The defibrillator 200 may optionally also have a sensor port 219 in the housing 201, which is also sometimes known as an ECG port. The sensor port 219 can be adapted for plugging in the sensing electrodes 209, which are also known as ECG electrodes and ECG leads. It is also possible that the sensing electrodes 209 can be connected continuously to the sensor port 219, instead. The sensing electrodes 209 can be types of transducers that can help sense an ECG signal, e.g. a 12-lead signal, or a signal from a different number of leads, especially if they make good electrical contact with the body of the patient and in particular with the skin of the patient. In embodiments, the ECG signals occasionally include pacing artifacts arising from the pacing signals that are occasionally emitted from the implanted heart pacing device 87. As with the defibrillation electrodes 204, 208, the support structure can be configured to be worn by the patient 282 so as to maintain the sensing electrodes 209 on a body of the patient 282. For example, the sensing electrodes 209 can be attached to the inside of the support structure 170 for making good electrical contact with the patient 82, similarly with the defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin of the patient 82. Electrically speaking, when the fluid is deployed, the electrical impedance between each electrode and the skin is reduced. Mechanically speaking, the fluid may be in the form of a low-viscosity gel. As such, it will not flow too far away from the location it is released, after being deployed. The fluid can be used for both the defibrillation electrodes 204, 208, and for the sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. The fluid deploying mechanism 274 can be configured to cause at least some of the fluid to be released from the reservoir, and be deployed near one or both of the patient locations to which the electrodes 204, 208 are configured to be attached to the patient. In some embodiments, the fluid deploying mechanism 274 is activated prior to the electrical discharge responsive to receiving an activation signal AS from a processor 230, which is described more fully later in this document.

In some embodiments, defibrillator 200 also includes a measurement circuit 220, as one or more of its modules working together with its sensors or transducers. The measurement circuit 220 senses one or more electrical physiological signals of the patient from the sensor port 219, if provided. Even if the defibrillator 200 lacks a sensor port, the measurement circuit 220 may optionally obtain physiological signals through the nodes 214, 218 instead, when the defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance (IMP. or Z), which can be sensed between the electrodes 204, 208 and/or between the connections of the sensor port 219 considered pairwise. Sensing the impedance can be useful for detecting, among other things, whether these electrodes 204, 208 and/or the sensing electrodes 209 are not making good electrical contact with the patient's body at the time. These patient physiological signals may be sensed when available. The measurement circuit 220 can then render or generate information about them as inputs, data, other signals, etc. As such, the measurement circuit 220 can be configured to render a patient input responsive to a patient parameter sensed by a sensor. In some embodiments, the measurement circuit 220 can be configured to render a patient input, such as values of an ECG signal, responsive to the ECG signal sensed by the sensing electrodes 209. More strictly speaking, the information rendered by the measurement circuit 220 is output from it, but this information can be called an input because it is received as an input by a subsequent stage, device or functionality.

The defibrillator 200 also includes a processor 230. The processor 230 can be configured to perform any one or more of these operations described in this document. The processor 230 may be implemented in a number of ways. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 230 may include, or have access to, a non-transitory storage medium, such as a memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

The processor 230 can be considered to have a number of modules. One such module can be a detection module 232. The detection module 232 can include a Ventricular Fibrillation (VF) detector (not shown in FIG. 2). The patient's sensed ECG from measurement circuit 220, which can be available as inputs, data that reflect values, or values of other signals, may be used by the VF detector to determine whether the patient is experiencing VF. Detecting VF is useful, because VF typically results in SCA. The detection module 232 can also include a Ventricular Tachycardia (VT) detector for detecting VT (not shown in FIG. 2), and so on.

Another such module in processor 230 can be an advice module 234, which generates advice for what to do. The advice can be based on outputs of the detection module 232. There can be many types of advice according to embodiments. In some embodiments, the advice is a shock/no shock determination that the processor 230 can make, for example via the advice module 234. The shock/no shock determination can be made by executing a stored Shock Advisory Algorithm. A Shock Advisory Algorithm can make a shock/no shock determination from one or more ECG signals that are captured according to embodiments, and determine whether or not a shock criterion is met. The determination can be made from a rhythm analysis of the captured ECG signal or otherwise. For example, there can be shock decisions for VF, VT, etc.

In some embodiments, when the determination is to shock, an electrical charge is delivered to the patient. Delivering the electrical charge is also known as discharging and shocking the patient. As mentioned above, such can be for defibrillation, pacing, and so on.

In perfect conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in published US patent application No. US 2019/0030351 A1, and No. US 2019/0030352 A1, and which are incorporated herein by reference.

The processor 230 can include additional modules, such as the other module 236, for other functions. In addition, if the internal monitoring device 281 is indeed provided, the processor 230 may receive its inputs, etc.

The defibrillator 200 optionally further includes a memory 238, which can work together with the processor 230. The memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. The memory 238 is thus a non-transitory storage medium. The memory 238, if provided, can include programs for the processor 230, which the processor 230 may be able to read and execute. More particularly, the programs can include sets of instructions in the form of code, which the processor 230 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of the processor 230, and can also include protocols and ways that decisions can be made by the advice module 234. In addition, the memory 238 can store prompts for the user 282, if this user is a local rescuer. Moreover, the memory 238 can store data. This data can include patient data, system data and environmental data, for example as learned by the internal monitoring device 281 and the outside monitoring device 180. The data can be stored in the memory 238 before it is transmitted out of the defibrillator 200, or be stored there after it is received by the defibrillator 200.

As mentioned earlier in this document the ECG signals sensed by the sensing electrodes 209 occasionally include pacing artifacts that arise from the pacing signals that are emitted from the implanted heart pacing device 87. Embodiments detect these pacing artifacts and render pacing values from them. And, the processor 230 can be configured to be able to input any pacing values rendered from any such pacing artifacts that are actually detected, whether the pacing artifacts are detected in the sensed respective ECG signal portions or in the rendered ECG values of the ECG signal portions. Such detection can be performed in a number of ways according to embodiments.

In particular, in embodiments the WCD system also includes a pacing signal detection functionality 221. The pacing signal detection functionality 221 can be configured to detect any pacing artifacts that are actually included in the ECG signal portion. As later described with reference to FIG. 4, a sensed or detected ECG signal portion may or may not include pacing artifacts arising from the pacing signals occasionally emitted by the implanted heart pacing device 87. The pacing signal detection functionality 221 can be further configured to render, for input by the processor 230, pacing values from any such pacing artifacts. Such input can be external, or internal such as between successive stages of the processor 230.

The processor 230 may then attempt inputting any pacing values rendered that way. The attempt will be successful if pacing signals had indeed been emitted, and therefore the sensed or detected ECG signal portion did include pacing artifacts, for which pacing values had been rendered. An example of such success is ECG signal portions 422, 423 of FIG. 4. The attempt, however, will not be successful, i.e., it will fail, if no pacing signals had been emitted, and therefore the sensed or detected ECG signal portion did not include pacing artifacts, and therefore no pacing values had been rendered. An example of such failure is the previous ECG signal portion 421 of FIG. 4.

Detecting such pacing artifacts by can be performed in a number of ways. In embodiments, the pacing signal detection functionality can be configured to detect any sets of pacing artifacts included in the respective ECG signal portions by filtering the ECG signal portions for detecting possible pacing artifacts, then determining whether or not selected ones of the possible pacing artifacts meet a validation criterion; and confirming, responsive to the validation criterion being met, the selected possible pacing artifacts as the pacing artifacts.

The filtering can happen on portions of the ECG signal received from the sensor port 219 by filtering for voltages, or based on the values of the ECG signal by numerically filtering the values. In such cases, an analog to digital converter (ADC) may be used for the incoming ECG signal. For example, filtering can be for pacing artifacts with widths between approximately 0.1 msec and 2 msec, and with amplitudes between 0.4 mV and 1000 V. If the manufacturer, and the make and model of the implanted heart pacing device 87 are known, that may be a help, but not conclusively as a single pacing device may pace differently for different circumstances. For such embodiments, the pacing signal detection functionality may include an analog front end (AFE) chip such as the ADAS1000 chip available from Analog Devices, Inc. Norwood, USA.

In embodiments, the pacing artifacts are validated. For instance, a pacing artifact can be confirmed as not a QRS complex if it lacks features of one, for example no T-wave, no P, etc. Additionally, in embodiments, the pacing artifacts can be validated on the expectation of being periodic. For instance, the validation criterion may include that the possible pacing artifacts occur at regular time intervals, when taken in sequence.

The pacing signal detection functionality 221 can be implemented in a number of ways, and with selecting how to distribute its operations advantageously, given the already existing functionality for analyzing the ECG signal portions. In some embodiments, the pacing signal detection functionality 221 is implemented at least in part by the measurement circuit 220, or even exclusively by the measurement circuit 220. In some embodiments, the pacing signal detection functionality 221 is implemented at least in part by the processor 230, or even exclusively by the processor 230. In some embodiments, the pacing signal detection functionality 221 is implemented at least in part, or exclusively by a pacing detector module 222 that is distinct from the processor 230 and from the measurement circuit 220.

The defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, the communication module 290 may transmit wirelessly, e.g., on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. The module 290 may also include such interconnected sub-components as may be deemed necessary by a person skilled in the art, for example an antenna, portions of a processor, supporting electronics, outlet for a telephone or a network cable, etc.

The defibrillator 200 may also include a power source 240. To enable portability of the defibrillator 200, the power source 240 typically includes a battery. Such a battery is typically implemented as a battery pack, which can be rechargeable or not. Sometimes a combination is used of rechargeable and non-rechargeable battery packs. Other embodiments of the power source 240 can include an AC power override, for where AC power will be available, an energy-storing capacitor, and so on. Appropriate components may be included to provide for charging or replacing the power source 240. In some embodiments, the power source 240 is controlled and/or monitored by the processor 230.

The defibrillator 200 may additionally include an energy storage module 250. The energy storage module 250 can be coupled to the support structure of the WCD system, for example either directly or via the electrodes and their leads. The module 250 is where some electrical energy can be stored temporarily in the form of an electrical charge, when preparing it for discharge to administer a shock. In embodiments, the module 250 can be charged from the power source 240 to the desired amount of energy, for instance as controlled by the processor 230. In typical implementations, the module 250 includes a capacitor 252, which can be a single capacitor or a system of capacitors, and so on. In some embodiments, the energy storage module 250 includes a device that exhibits high power density, such as an ultracapacitor. As described above, the capacitor 252 can store the energy in the form of an electrical charge, for delivering to the patient.

A decision to shock can be made responsive to the shock criterion being met, as per the above-mentioned determination. When the decision is to shock, the processor 230 can be configured to cause at least some or all of the electrical charge stored in the module 250 to be discharged through the patient 82 while the support structure is worn by the patient 82, so as to deliver the shock 111 to the patient 82.

For causing the discharge, the defibrillator 200 moreover includes a discharge circuit 255. When the decision is to shock, the processor 230 can be configured to control the discharge circuit 255 to discharge through the patient at least some of all of the electrical charge stored in the energy storage module 250, especially in a desired waveform. Discharging can be to the nodes 214, 218, and from there to the defibrillation electrodes 204, 208, so as to cause a shock to be delivered to the patient. The circuit 255 can include one or more switches 257. The switches 257 can be made in a number of ways, such as by an H-bridge, and so on. The circuit 255 could also be thus controlled via the processor 230, and/or the user interface 280.

A time waveform of the discharge may be controlled by thus controlling the discharge circuit 255. The amount of energy of the discharge can be controlled by how much energy storage module has been charged, and also by how long the discharge circuit 255 is controlled to remain open.

The defibrillator 200 can optionally include other components.

Figure 3:
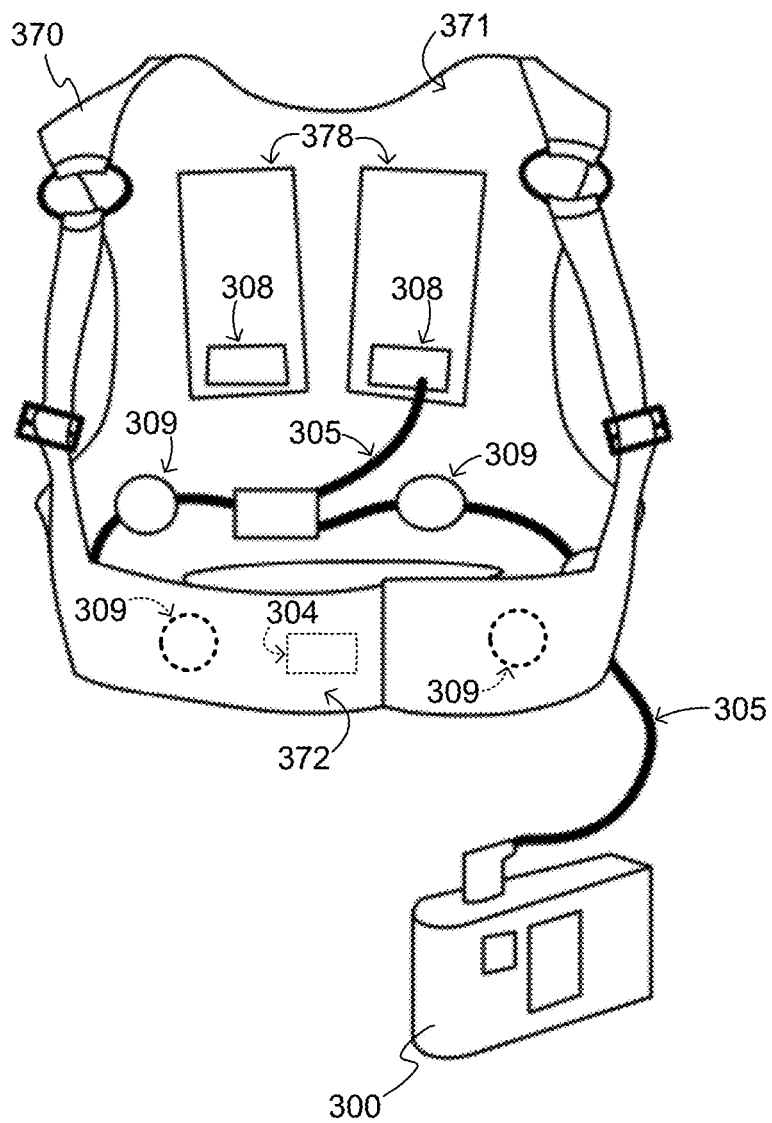
FIG. 3 is a diagram of sample embodiments of components of a WCD system.

FIG. 3 is a diagram of sample embodiments of components of an WCD system. A support structure 370 includes a vest-like wearable garment. The support structure 370 has a back side 371, and a front side 372 that closes in front of the chest of the patient.

The WCD system of FIG. 3 also includes an external defibrillator 300. FIG. 3 does not show any support for external defibrillator 300, which may be carried in a purse, on a belt, by a strap over the shoulder, on the support structure 370, and so on. Wires 305 connect the external defibrillator 300 to electrodes 304, 308, 309. Of those, the electrodes 304, 308 are defibrillation electrodes, and the electrodes 309 are ECG sensing electrodes.

The support structure 370 is configured to be worn by the ambulatory patient so as to maintain the electrodes 304, 308, 309 on a body of the patient. Indeed, the back defibrillation electrodes 308 are maintained in pockets 378. Of course, the inside of the pockets 378 can be made with loose netting, so that the electrodes 308 can contact the back of the patient, especially with the help of the conductive fluid that has been deployed. In addition, the sensing electrodes 309 are maintained in positions that surround the patient's torso, for sensing ECG signals and/or the impedance of the patient.

ECG signals in a WCD system may include too much electrical noise to be useful. To ameliorate the problem, multiple ECG sensing electrodes 309 are provided, for presenting many options to the processor 230. These options are different vectors for sensing the ECG signal, as described now in more detail.

It is desired to sense the patient's ECG signal as well as possible, for measuring its parameters. If only one source of the ECG signal is available, then that is the one that is used. The arrangement of FIG. 3, however, shows four sensors 309. These define pairwise six vectors, each with a channel, which give more options. An example is now described.

Figure 4:
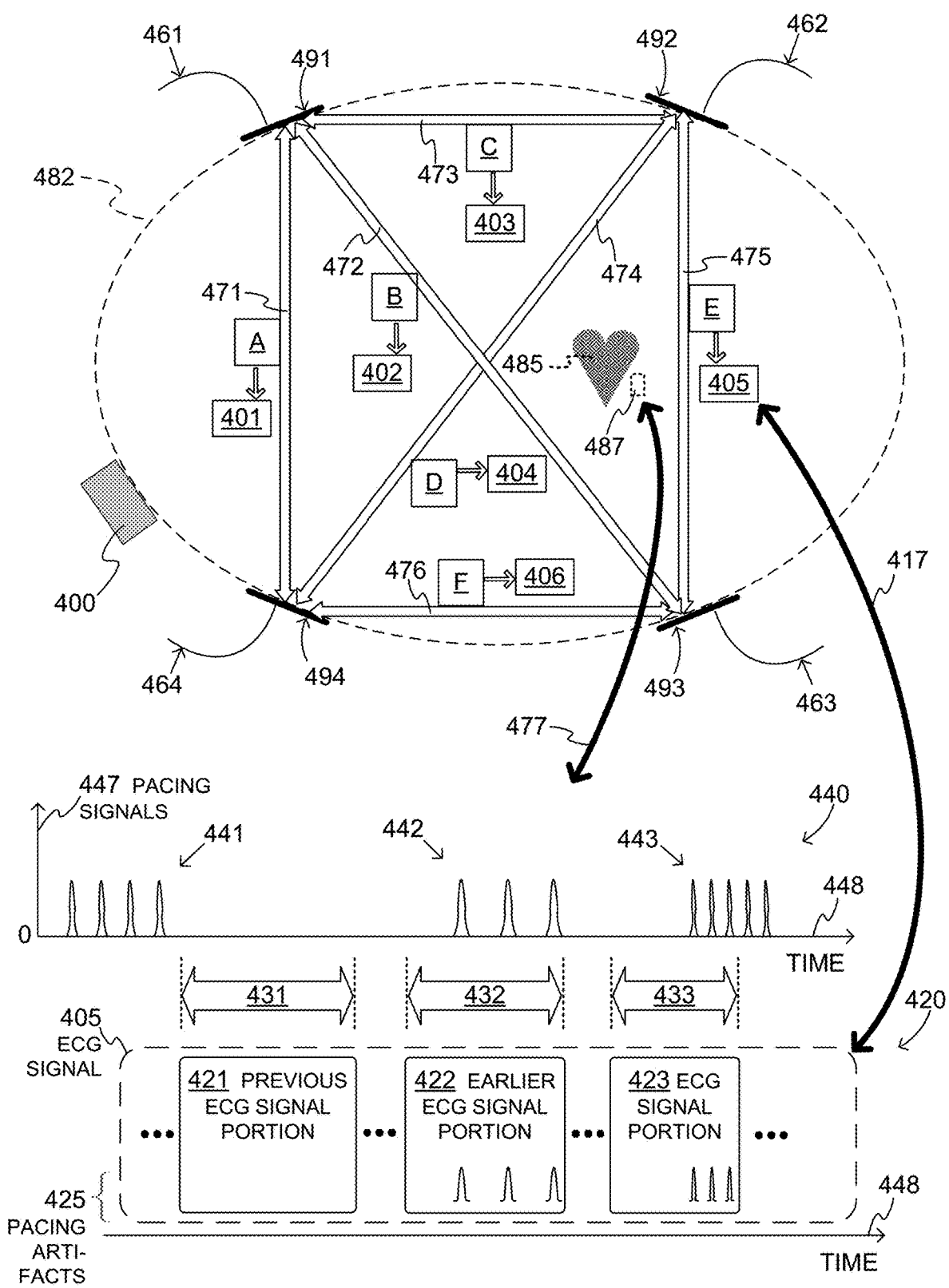
FIG. 4 is a conceptual diagram for illustrating an example of how a defibrillator of a WCD system according to embodiments can be used with multiple electrodes for sensing ECG signals along different vectors, while at the same time showing a heart pacing device implanted in the patient that occasionally emits pacing signals, which ultimately give rise to pacing artifacts in the sensed ECG signals.

FIG. 4 is a conceptual diagram for illustrating an example how a defibrillator of a WCD system according to embodiments can use multiple electrodes for sensing ECG signals along different vectors. A section of a patient 482 having a heart 485 is shown. In FIG. 4, the patient 482 is viewed from the top, the patient 482 is facing downwards, and the plane of FIG. 4 intersects the patient 482 at the torso of the patient. The defibrillator 400 is shown attached to the patient 482.

Four ECG sensing electrodes 491, 492, 493, 494 are maintained on the torso of the patient 482, and have respective wire leads 461, 462, 463, 464. It will be recognized that the electrodes 491, 492, 493, 494 surround the torso, similarly with the sensing electrodes 309 in the example of FIG. 3. The wire leads 461, 462, 463, 464 typically are connected to the defibrillator 400, except that is not shown in FIG. 4 to reduce the clutter and improve readability.

In FIG. 4 it will be understood that the ECG sensing electrodes 491, 492, 493, 494 are drawn as if they were on the same plane. This is done because simplicity of explanation is preferred but, strictly speaking, it is not necessarily the case. In fact, the electrodes 491, 492, 493, 494 might not always be on the same vertical plane. And, the defibrillator 400 is not necessarily on the same vertical plane as the electrodes 491, 492, 493, 494.

Any pair of the four ECG sensing electrodes 491, 492, 493, 494 defines a vector, along which an ECG signal may be sensed and/or measured. As such, the four electrodes, also known as sensors 491, 492, 493, 494 pairwise define six vectors 471, 472, 473, 474, 475, 476. FIG. 4 thus illustrates a multi-vector embodiment. Although four electrodes, and thus six vectors, are shown in the example of FIG. 4, other numbers of sensors and corresponding vectors can be implemented. And, of course, if the electrodes 491, 492, 493, 494 are not on the same vertical plane, the vectors 471, 472, 473, 474, 475, 476 are not necessarily on the same plane, either.

These vectors 471, 472, 473, 474, 475, 476 have respective channels A, B, C, D, E, F. ECG signals 401, 402, 403, 404, 405, 406 may thus be sensed and/or measured from the channels A, B, C, D, E, F, respectively, and in particular from the appropriate pairings of the wire leads 461, 462, 463, 464 for each channel. The ECG signals 401, 402, 403, 404, 405, 406 may be sensed concurrently or not.

In such embodiments, a WCD may assess which of the channels A, B, C, D, E, F provides the best ECG signal for rhythm analysis and interpretation. Or, instead of using only one channel, a WCD may determine that it can keep two or more but not all of the channels and use their ECG signals, for instance as described in U.S. Pat. No. 9,757,581.

In such embodiments, the measurement circuit 220 can be configured to render respective sets of ECG values for the respective ECG signals, one set for each signal. In such cases, the pacing signal detection functionality 221 can be configured to detect any sets of pacing artifacts included in the respective ECG signal portions, and to render sets of pacing values from the sets of the pacing artifacts for input by the processor. In other instances, instead of sets, a single ECG signal is considered, a single set of ECG values and of pacing values, and so on.

In FIG. 4, the patient 482 has an implanted heart pacing device 487, which is configured to occasionally emit pacing signals. An arrow 477 bridges the heart pacing device 487 with a diagram 440 that shows sample such pacing signals.

The diagram 440 has a vertical axis 447 for indicating amplitude of pacing signals, and a time axis 448 that shows when the pacing signals are emitted. In terms of waveform, in this example all the pacing signals are shown as monophasic, rising from the zero value of the axis 448 to a peak value and then returning to the zero value. The pacing signals instead could be biphasic, for example falling from the peak value to a negative value before returning to the zero value.

In the diagram 440, three sets of pacing signals 441, 442, 443 are shown as emitted. It is noteworthy that the number of pacing signals within each of the sets 441, 442, 443 is different. In particular, the set 441 has four pacing signals, the set 442 three, and the set 443 five. Also, the frequency or time rate of these pacing signals is not the same from one set to the next. In particular, in the set 441 they happen at a medium time rate, in the set 442 at a slower time rate, and in the set 443 at a faster time rate. Here the amplitudes of the pacing signals are shown as all being similar, while that is not necessarily the case. It will be understood that the pacing pulses in diagram 440 are quick, i.e., short in duration, i.e., narrow along the horizontal time axis 448. For instance, they may last 0.4 msec, and therefore be at the equivalent frequency of 2.5 kHz. As such, to detect the pacing pulses, sampling may be need to be performed at a frequency of at least 4 kHz. This is 8 times faster than the present 500 Hz sampling speed needed to detect the ECG signals alone. As such, sampling for detecting the pacing artifacts consumes more computational resources.

In FIG. 4, the pacing signals of FIG. 4 are shown as emitted from the heart pacing device 487. In embodiments, these pacing signals give rise to pacing artifacts to the sensed ECG signals. In other words, the pacing signals of FIG. 4 distort the sensed ECG signals accordingly by producing respective pacing artifacts. This is now illustrated also graphically.

An arrow 417 bridges the ECG signal 405 from the channel E with a diagram 420 intended for plotting conceptually aspects of the ECG signal 405. In the diagram 420, three ECG signal portions are identified, namely an ECG signal portion 423, an earlier ECG signal portion 422 that occurs before the ECG signal portion 423, and a previous ECG signal portion 421 that occurs before the ECG signal portion 421. According to embodiments, such ECG signal portions 421, 422, 423 are what can be analyzed for determining whether or not an alert criterion is met, for making a shock/no shock decision, and so on. However, the sample ECG signal portions of FIG. 4 are not necessarily the portions of the ECG signal that are segmented for analysis. For instance, the earlier ECG signal portion 422 could be taken up for analysis concurrently with the ECG signal portion 423, or earlier from it, often depending on how much earlier an analysis was performed.

The diagram 420 has a time axis 448, which is the same as of the diagram 440, and which indicates that items of each of these diagrams are considered synchronized, subject to second-order effects described later in this document. The ECG signal portions 421, 422, 423 occur during time durations 431, 432, 433 respectively. These also determine which ones of the pacing signals of the diagram 440 will become pacing artifacts 425 in the ECG signal portions 421, 422, 423 in the diagram 420. As can be seen, the ECG signal portion 423 has only three pacing artifacts from those in the set 443, the ECG signal portion 422 has all three pacing artifacts of the set 442, and the ECG signal portion 421 has no pacing artifacts. This is an example of what was mentioned previously, namely that the ECG signal portion that is sensed or detected and subsequently may or may not include pacing artifacts arising from the pacing signals that are occasionally emitted by the implanted heart pacing device 487. And, in embodiments, the WCD system does not know when the heart pacing device 487 is emitting its pacing signals, such as in the sets 441, 442, 443. Even more confoundingly, such pacing signals may appear like noise. Further complicating matters, a QRS complex of a patient that is induced by a pacing signal, which is also called a paced QRS complex, is often different than a spontaneous QRS complex of the patient; in fact, a paced QRS complex can have a lesser amplitude than a spontaneous QRS complex, in which case its QRS complex may be more easily confused with noise. In embodiments, paced QRS complexes are detected with further adjustments.

In embodiments, the WCD system detects the pacing artifacts 425, from which it infers the pacing signals 447, and operates accordingly. Detecting the pacing artifacts 425 can be as described above from the pacing signal detection functionality 221. In diagram 420 the pacing artifacts 425 are shown this way only for purposes of preserving fidelity with how the corresponding pacing signal are shown above them, in diagram 440. However, and as written above, since the pacing signals 447 are much shorter in duration than the features of the ECG signal portions 421, 422, 423, the pacing artifacts 425 themselves will not appreciably distort the ECG signals, when they are viewed when viewed in relation to the underlying corresponding concurrent ECG signals. In fact, given how much shorter the pacing signals and the pacing artifacts are than features of the ECG signals, the pacing signals and/or the pacing artifacts can be represented as pacing values, as also written elsewhere in this document. In fact, these pacing values can be represented as pacing markers occurring at specific times. For instance, a pacing value can be represented by a vector having two values, for instance, [(time instant of pacing pulse), (marker showing that pacing pulse occurred at that time instant)].

Figure 5:
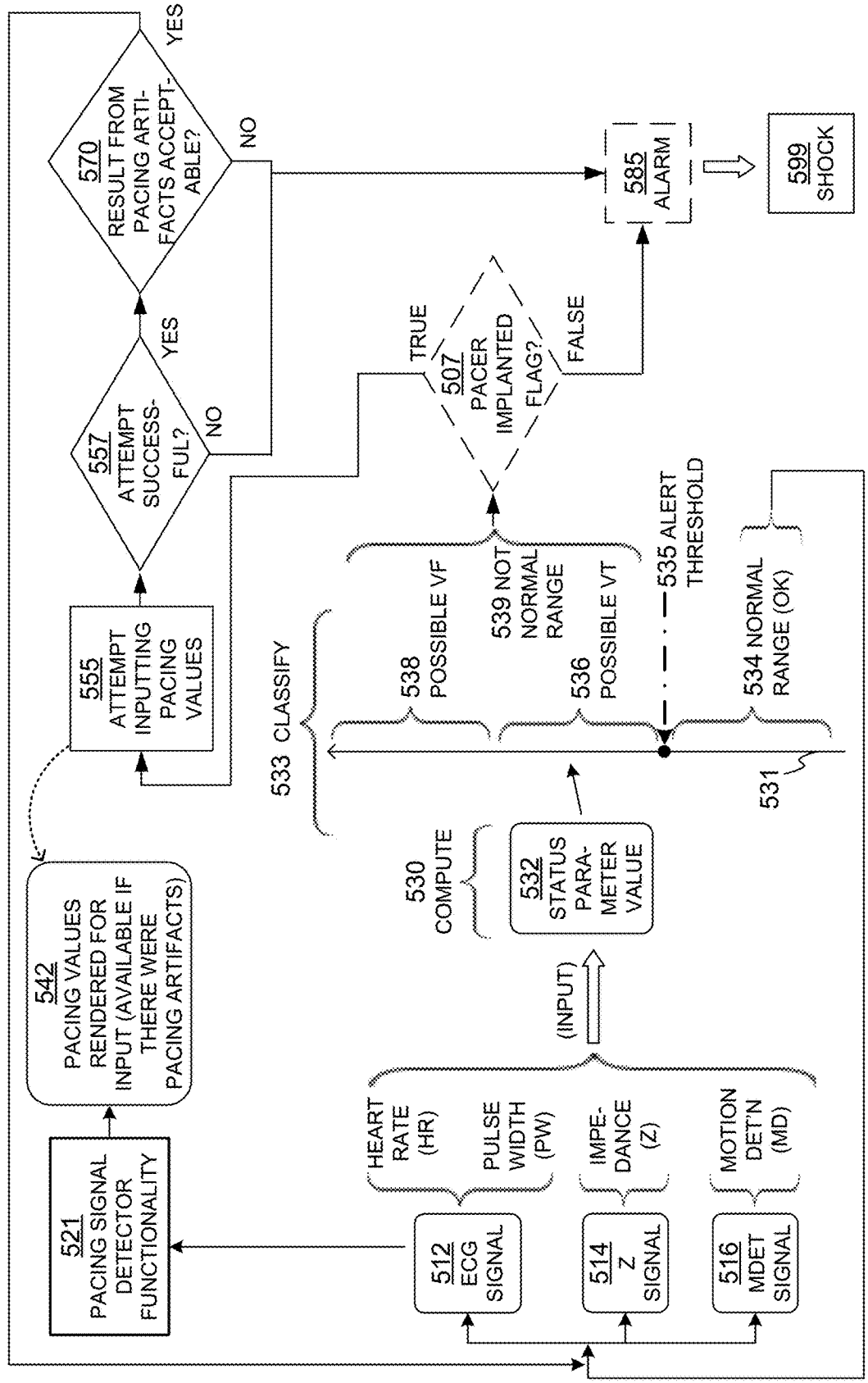
FIG. 5 is a mind map for describing sample operations according to embodiments.

FIG. 5 is a mind map for describing sample operations according to embodiments. Many of these operations may be performed by the processor 230.

Starting at the bottom left of FIG. 5, various signals may be used in embodiments. For instance, the patient's ECG signal 512, impedance signal (Z) 514 and a motion detection signal (MDET) 516 may be used. These signals may be available as signals or as values of signals.

From such signals, or their values, various patient parameters may be extracted. For example, a heart rate (HR) value and/or a pulse width (PW) value may be computed from the ECG values of the ECG signal 512, an impedance (Z) value may be extracted from the impedance signal (Z) 514, and a motion profile of the patient may be inferred from the motion detection signal (MDET) 516. For instance, the heart rate (HR) value may be computed by the processor 230 first identifying QRS complexes in the ECG signal portion or in the ECG values, and then determining the time rate of the taller R-peaks. For another instance, the processor 230 can be further configured to identify a QRS complex in the ECG signal portion or in the rendered ECG values, measure a pulse width (PW) of the identified QRS complex, and compute the value for the status parameter also from the measured pulse width.

It may then be determined whether or not an alert criterion is met. The determination may be from at least the HR value, but it may also be from the PW value, the impedance (Z) value and the motion profiled that is quantified. In many embodiments, this alert criterion is only an internal one, and the patient is not necessarily notified even if the alert criterion is met.

In some embodiments, the determination is made by computing, according to an operation 530, a value 532 for a status parameter, which is also known as a status parameter value 532. In some embodiments, the status parameter value 532 takes into account the heart rate value, for instance the status parameter value 532 can be computed from the HR value. Then according to an operation 533, the computed status parameter value 532 can be classified according to its value. It can be determined whether or not the alert criterion is met from whether the computed value 532 for the status parameter exceeds an alert threshold 535. This relationship is by plotting a vertical axis 531, indicating on it a point for the alert threshold 535, and plotting on it the status parameter value 532.

In this example, if the value of the status parameter value 532 is less than the alert threshold 535, then it belongs in a normal range 534 that is below the alert threshold 535. Then execution can return to gathering new segments or portions of the ECG signal 512, the impedance signal (Z) 514 and the motion detection signal (MDET) 516. If the patient is and remains fine, the status parameter value 532 will have values in the normal range 534, and the WCD system will be monitoring indefinitely.

If, according to the operation 533, the computed status parameter value 532 has a value higher than the alert threshold 535, then it belongs in a not normal range 539 that is above the alert threshold 535. This not normal range 539 may have a subrange 536 for possible ventricular tachycardia (VT), another subrange 538 for possible ventricular fibrillation (VF), and so on. Such can be a cause for concern about the patient.

In prior art, when the computed status parameter value 532 belongs in the not normal range 539, execution proceeds to an operation 585 where alarms maybe sound for the patient, then where it may be determined (not shown) whether or not a final shock criterion is met, and finally to an operation 599 where a shock is delivered due to the final shock criterion being met. A problem, however, is that the value 532 belonging in the not normal range 539 could be a false positive; in fact, there was no reason for alarm. Alarms due to false positives annoy the patient.

In embodiments, however, it may be checked whether such false positives arise from effects of pacing signals, which could or could not be emitted at the time by the implanted heart pacing device 87. For this checking, a pacing signal detection functionality 521 is provided, which could be as described for functionality 221. In some embodiments, the outputs of the pacing signal detection functionality 521 are attempted to be input always, if the status parameter value 532 belongs in the not normal range 539, as described in more detail below.

In other embodiments, however, a WCD system can be made for both patients that have or do not have an implanted heart pacing device. In addition, such a WCD system could further have a pacer implanted flag, which can be configured to have values of at least true and false. At the time the WCD system is planned for a patient, that flag can be set to a value of true or false, for example using the programming interface, because at the time it is known whether or not the patient indeed has an implanted heart pacing device. Strictly speaking, a starting value for such a WCD system can be an additional possible value of "YET_UNKNOWN", which can be set to true or false upon fitting the patient with the WCD system.

An advantage of including the pacer implanted flag is that a single system can be used for different patients. The pacer implanted flag can be implemented in a number of ways. One such way is by a data structure, such as one or more registers in a memory. For instance, as seen briefly in FIG. 6, the value of "TRUE" can be stored in one or more register of memory 638, as a pacer implanted flag 607. (Of course, the registers may maintain values such 11 for TRUE, 10 for FALSE, 00 for YET_UNKNOWN and so on.) Another way is by suitable implementation of a state machine for the whole processor, and so on.

Returning to FIG. 5, in such embodiments, according to an operation 507, the value of the pacer implanted flag is determined. The outputs of the pacing signal detection functionality 521 can be attempted to be input only responsive to the pacer implanted flag having a value of true, as would be the case for patient 82. But, if the pacer implanted flag turns out to have a value of false, the outputs of the pacing signal detection functionality 521 can be ignored, and it can be instead determined whether or not a default shock criterion is met, and so on. It will be understood, then, that the operation 507 will not be performed in embodiments where the flag is not provided. In such embodiments a no answer is not contemplated, and the execution proceeds in the direction pointed to by the yes answer of the operation 507. There can be alternate characterizations, such as using a value of NOT_FALSE, and so on.

Regarding the outputs of the pacing signal detection functionality 521: this functionality 521 may render pacing values 542 for input by the processor 230, if pacing artifacts have been detected as actually included in the ECG signal portion 512.

According to an operation 555, which can be engaged if the pacer implanted flag has the value of true, it can be attempted to input any such pacing values 542. According to another operation 557, it can be determined whether or not the attempt of operation 555 was successful, meaning such pacing values were actually input because they had actually been detected. If not, then execution can proceed to operations 585 for alarm, 599 for shock, and so on.

If, however, at the operation 557 it is determined that yes, the attempt of operation 555 was successful then, according to an operation 570, it can be determined whether or not the results from the detected pacing artifacts were acceptable. This can be performed in a number of ways, and also as is described later in this document. If at the operation 570 the answer is no, then execution can proceed to operations 585 for alarm, 599 for shock, and so on.

If, however, at the operation 570 the answer is yes, then crossing the alert threshold 535 was a false positive, and the patient need not be alarmed. Instead, execution can then return to gathering new segments or portions of the ECG signal 512, the impedance signal (Z) 514 and the motion detection signal (MDET) 516. All this will have been accomplished because the very first alert criterion, while it was due cause for additional internal investigation for the event of a problem with the patient, it was not cause—yet—to distract the patient by alarming them, alerting them, or even informing them.

In embodiments, a WCD system may identify a preferential or preferred channel among its available channels. The channel is preferential or preferred in that it is easier to identify pacing artifacts within it, which is what happens when the patient 82 has the implanted heart pacing device 87. Such a channel may be different than a channel that may have been identified as having less noise for reading the ECG signal. And, when the time comes for attempting to detect pacing artifacts, the WCD system first tries to use the previously identified channel. In such embodiments, the preferential channel can be identified based on which of the channels the pacing artifacts are more easily detected. In some of these embodiments, the identified channel is stored in a way that it can be easily retrieved. Examples are now described.

Figure 6:
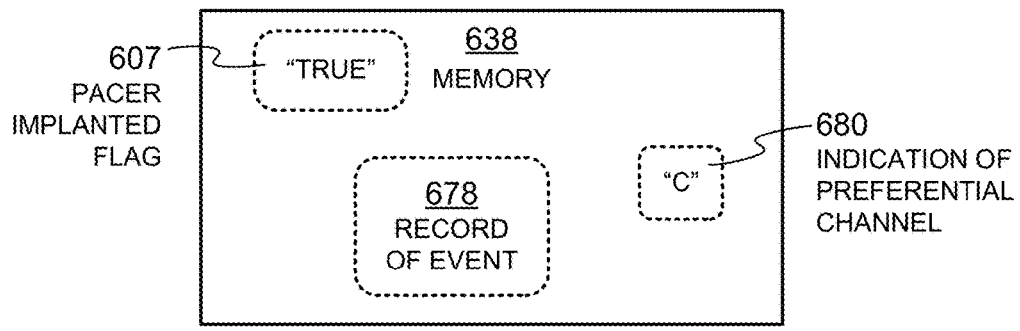
FIG. 6 is a block diagram of a memory with sample contents, according to embodiments.

In some embodiments, the WCD system further includes a memory, such as the memory 238. In such embodiments, an indication of the preferential channel that has been previously identified has been stored in the memory. For instance, FIG. 6 is a block diagram of a memory 638, which can be the memory 238. In this example, the memory 638 has, as sample contents, a record 678 of a previous event that has been written for later review, and an indication 680 of the preferential channel "C". That channel C is shown in FIG. 4 as being in vector 473 that is defined by the pair of the electrodes 491 and 492.

In such embodiments, while referring to multiple diagrams now, when it is attempted to input preferential pacing values, such as the values 542 of FIG. 5, which have been rendered from the pacing signal detection functionality 221 or 521, an included operation may be to read the stored indication 680 from the memory 638.

Figure 7:
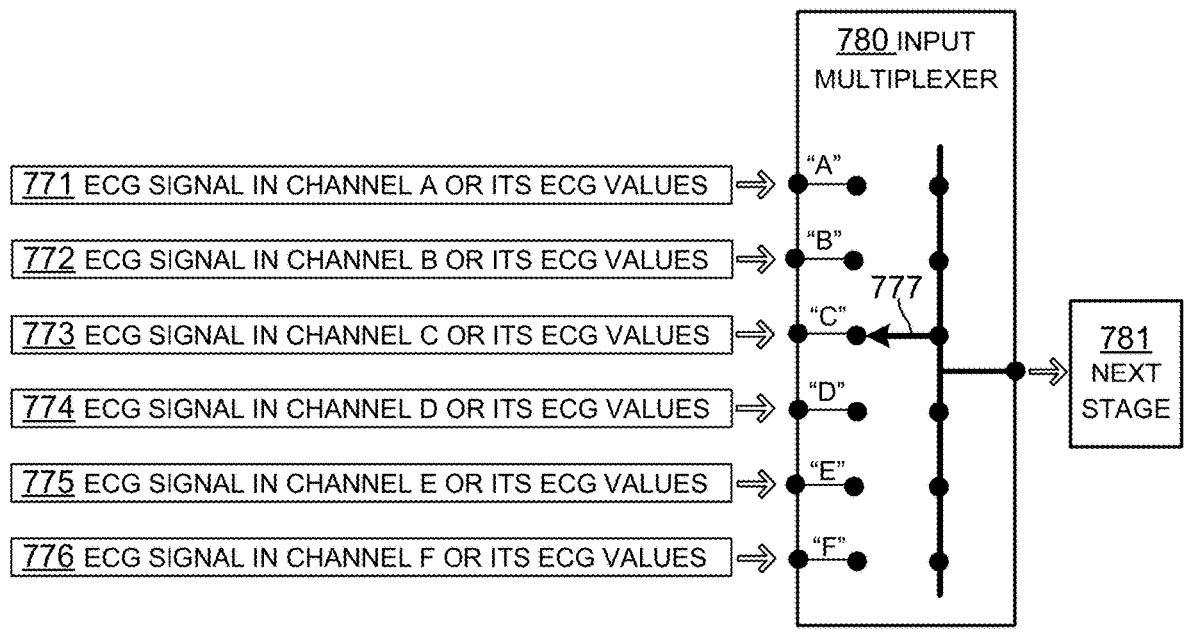
FIG. 7 is a diagram of sample input multiplexer made according to embodiments, which is receiving sample ECG signals, such as the ECG signals of FIG. 4.

In some embodiments, the preferential channel is selected in a different way. In particular, and as seen in the example of FIG. 7, a WCD system and/or its processor may include multiple stages, of which an input multiplexer 780 and a next stage 781 are shown. The input multiplexer 780 can be configured to receive, for each of the channels A, B, C, D, E, F, either the respective ECG signals of the respective channels or the respective ECG values of the respective channels 771, 772, 773, 774, 775, 776. The input multiplexer can be adjusted as shown by a selector 777, so that it passes only one of these inputs to the next stage 771. As such, there is no need to look up in memory. The selector 777 can be implemented in hardware for the signal or in software, and so on. In this example, the selector 777 has been adjusted to select channel C. In embodiments, the input multiplexer 780 is adjusted so that only the received ECG signal or the ECG values of the preferential channel are advanced to the next stage 781. A hardware implementation can be, for instance, by turning on appropriate switches such as transistors, while turning off others, to ensure that only the ECG signal 773 reaches the next stage 781.

In such embodiments, when it is attempted to input preferential pacing values, such as the values 542 of FIG. 5, an included operation may be for the next stage 781 to receive the received ECG signal or the ECG values from the input multiplexer 780.

The devices and/or systems mentioned in this document may perform functions, processes, acts, operations, actions and/or methods. These functions, processes, acts, operations, actions and/or methods may be implemented by one or more devices that include logic circuitry. A single such device can be alternately called a computer, and so on. It may be a standalone device or computer, such as a general-purpose computer, or part of a device that has and/or can perform one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description may include flowcharts, display images, algorithms, and symbolic representations of program operations within at least one computer readable medium. An economy may be achieved in that a single set of flowcharts can be used to describe both programs, and also methods. So, while flowcharts describe methods in terms of boxes, they may also concurrently describe programs.

Methods are now described.

Figure 8:
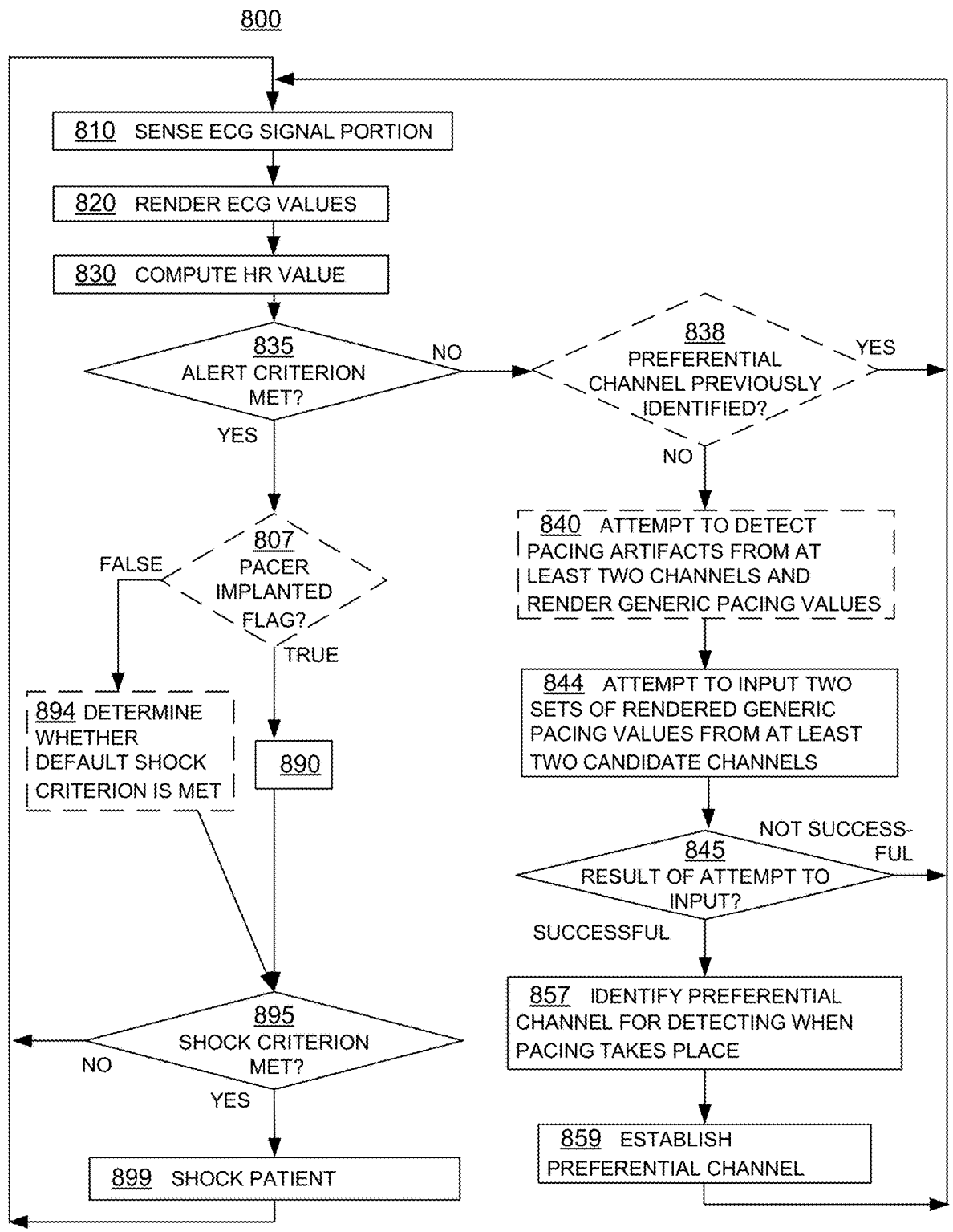
FIG. 8 is a flowchart for illustrating sample methods according to embodiments.

FIG. 8 shows a flowchart 800 for describing methods according to embodiments. According to an operation 810, ECG signal portions along different channels may be sensed, for example by sensors as described above.

According to another operation 820, sets of ECG values for the respective ECG signal portions can be rendered. This can be performed as described above, for example by a measurement circuit.

According to another operation 830, a heart rate (HR) value may be computed from at least one of the sets of the ECG values. This can be performed as described above.

According to another operation 835, it may be determined, from at least the HR value, whether or not an alert criterion is met. This can be performed as described above.

If, at the operation 835, the answer is yes then, according to an optional next operation 807, it may be determined what is the value of the pacer implanted flag, assuming the flag is provided and has been set to true or false. Everything written above about operation 507 of FIG. 5 applies also to operation 807, from which embodiments would have it, to how such embodiments would implement it, and so on.

If, at the operation 807, the answer is true, it means that the WCD system knows that this patient has an implanted heart pacing device, which could be emitting pacing signals. Then a group 890 of operations can be performed, which are described later in this document with reference to FIG. 9. These operations of group 890 end up with determining whether or not a shock criterion is met. Then execution proceeds to an operation 895.

If, at the operation 807, the answer is false, it means that the WCD system knows that this patient does not have an implanted heart pacing device in the first place. According to a next operation 894, it may be determined whether or not a default shock criterion is met, one that does not take into account the outputs of the pacing signal detection functionality 221, 521. Then execution again proceeds to the operation 895.

According to the operation 895, it may be inquired whether or not a shock criterion is met. Of course, which shock criterion will depend on which path the operation 895 was arrived from. If from operation 894, then the shock criterion is the default shock criterion of operation 894. If from group 890, then accordingly.

If, at the operation 895, it is learned that the applicable shock criterion is met then, according to another operation 899, the stored electrical charge can be caused to be discharged via the electrodes through the ambulatory patient 82 so as to deliver the shock 111 to the ambulatory patient 82. However, responsive to the applicable shock criterion not being met, no electrical charge is caused to be thus discharged responsive to this ECG signal portion. After that, the execution may again return to the operation 810 for sensing another portion of the ECG signal, and so on with monitoring the patient 82.

In particular, resulting from operation 807, the processor 230 can be further configured to attempt the inputting of any of the pacing values rendered from the pacing signal detection functionality 221, 521, only responsive to the pacer implanted flag having a value of true, but, responsive to the pacer implanted flag having a value of false, not so attempt and instead determine whether or not the default shock criterion is met and responsive to the default shock criterion being met, cause at least some of the stored electrical charge to be discharged via the electrode through the ambulatory patient so as to deliver a shock to the ambulatory patient, but not cause any electrical charge to be thus discharged responsive to the default shock criterion not being met.

Before completing the description of the remaining operations shown in FIG. 8, the group 890 of operations is now described in more detail with reference to FIG. 9.

Figure 9:
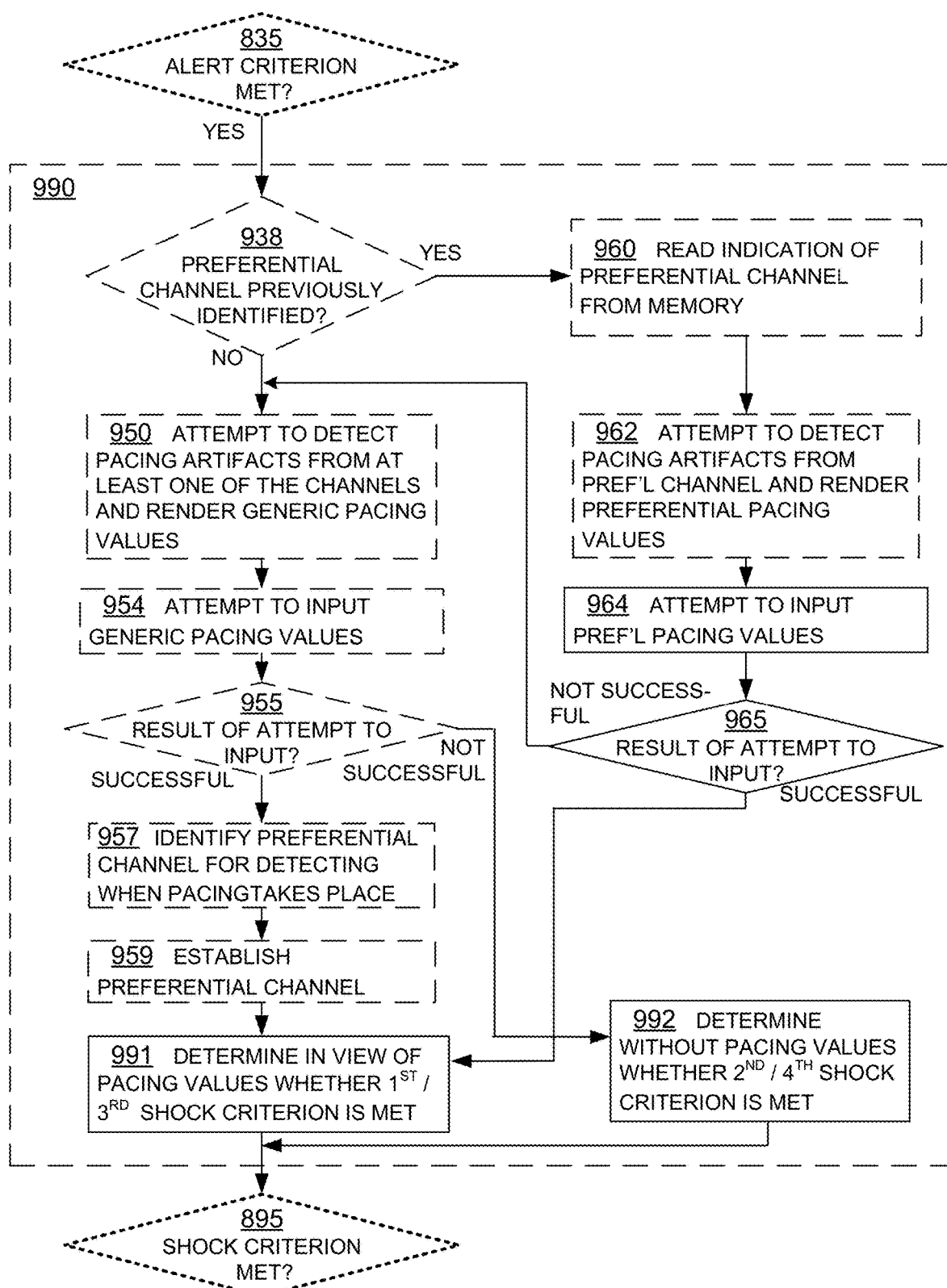
FIG. 9 is a flowchart for illustrating sample methods for performing a group of operations of the flowchart of FIG. 8 according to embodiments.

FIG. 9 shows a group 990 of operations that can be embodiments for the group 890 of operations. In addition, and for better reference, FIG. 9 repeats in dotted lines the above-described operations 835 and 895 of FIG. 8. Also, if the operation 807 is indeed performed after the operation 835, the group 890 would follow the path of true after the operation 807.

According to an operation 938, it can be optionally inquired whether or not a preferential one of the channels has been previously identified. In fact, it can be first determined whether or not the preferential one of the channels has been previously identified, before the inquiry of operation 938.

It should be noted that at the operation 938 the default answer is yes meaning, if the operation 938 is not performed, the execution follows the direction of the answer being yes. In particular, in some embodiments the answer is always yes, for instance if the preferred channel has been established at the time of fitting the WCD system to the patient. In such embodiments, the operation 938 might not be performed as a separate inquiry at all if the answer has been built in previously, for example by having adjusted the input multiplexer 777. In other embodiments, the operation 938 is performed if required as a separate inquiry, as a separate lookup, and where it is contemplated that the answer could be no.

Briefly if, at the operation 938 the answer is yes, then it will be attempted to read from the preferential channel for ultimately making a shock/no shock determination. If that attempt fails, then the path will be similar to if the answer were no in the first place, and any or another channel can be used.

In particular if, at the operation 938 the answer is yes then, per an optional operation 960, an indication such as the indication 680 can be read from the memory. Alternately, the operation 960 might not be needed, if the preferential channel has been selected by an input multiplexer.

According to another, optional operation 962, it may be attempted to detect pacing artifacts from the preferential channel, and render preferential pacing values from such artifacts. These pacing values are called preferential because, if they are indeed rendered, they would be from the preferential channel. Such may be performed as described above, for example by the pacing signal detection functionality 221, 521.

According to another operation 964, it may then be attempted to input any such preferential pacing values rendered from the pacing signal detection functionality of the preferential channel. This can be performed similarly with operation 555 of FIG. 5.

According to another operation 965, it can be inquired whether or not the operation 964 was successful or not. If successful then, according to another operation 991, it may be determined in view of the preferential pacing values whether or not a first shock criterion is met. Of course, it is understood that this determination of the operation 991 can be based on the preferential pacing values and other results that they produce, such as paced QRS complexes and so on. Then execution may proceed to operation 895 as per the above.

If, however, at the operation 965, it is answered that the operation 964 was not successful then, according to another, optional operation 950, it may be attempted to detect pacing artifacts from any one of the channels, and render generic pacing values from such artifacts. These pacing values are called generic because, if they are indeed rendered, they would be from any other channel, not the preferential one. Such may be performed as described above, for example by the pacing signal detection functionality 221, 521.

According to another, optional operation 954, it may then be attempted to input any such generic pacing values rendered by the operation 950. This can be performed similarly with operation 555 of FIG. 5.

According to another operation 955, it can be inquired whether or not the operation 954 was successful or not. If not successful then, according to another operation 992, it may be determined without any pacing values whether or not a second shock criterion is met. The second shock criterion can be as the default criterion of operation 894, or different. Then execution may proceed to operation 895 as per the above.

If, however, at the operation 955, it is answered that the operation 954 was successful, then execution may proceed to operation 991 for which, however, it is determined in view of the generic pacing values whether or not a third shock criterion is met. In some embodiments, the third shock criterion is the same as the first shock criterion, but that is not necessarily the case. Shock criteria, such as the first, second, third, fourth, default etc., can be numerical threshold values on a scale, above which there is a decision to shock and below which there is a decision to not shock.

In fact, in conjunction with the operation 954 being successful, according to another, optional operation 957, a preferential channel for detecting pacing may be identified. This can be by comparing channels, or by simply choosing one that worked, until an opportunity arises for a further refinement. It is notable that, at the operation 957, the identification is likely useful because it was made at a time of actual stress of the patient, given that the alert criterion had been met. And, according to another, optional operation 959, the preferential channel may be established responsive to having been identified. Establishing may be performed by the processor being further configured to store in the memory an indication of the identified candidate channel as the preferential one of the channels as shown in FIG. 6. Or, Establishing may be performed by the processor being further configured to adjust the input multiplexer to advance to the next stage only the received ECG signal or the ECG values of the preferential channel, as shown in FIG. 7. And so on.

If, at the operation 938, the answer is no then any one of operations 950, 954, 955, 957, 991 and 992 may be performed. In some embodiments, if operation 992 is performed having arrived at it via this path, it may be determined whether or not a fourth shock criterion is met, and so on. The fourth shock criterion may be the same as the second shock criterion, but that is not necessary.

Returning to FIG. 8 if, at the operation 835 it is determined that the alert criterion is not met, then there is likely no cause for alarm. A shock to the patient will not result based on the ECG signal portion that was thus analyzed at the earlier operations of this flowchart. Nevertheless, in some embodiments, the opportunity is used to try to identify, and store and establish, a preferential channel for later, in the event that the alert criterion might not be met later.

As such, if at the operation 835 the answer is no then, according to an operation 838, it can optionally be inquired whether or not a preferential one of the channels has been previously identified. This may be performed similarly with the operation 938; in fact, the operation 838 is optional at least in the same sense as the operation 938. In other words, at the operation 838 the default answer is yes meaning, if the operation 838 is not performed, the execution follows the direction of the answer being yes.

As a caution, operation 838 may be performed only if the pacer implanted flag has a value of true, else the execution may return to the operation 810. In other words, the operation 807 can be repeated immediately prior to operation 838, except that was not drawn so as not to clutter the drawing.

If at the operation 838 the answer is yes, then the execution may return to the operation 810 for sensing another portion of the ECG signal, since it is not needed to identify a preferential channel.

If, however, at the operation 838 the answer is no, then according to another, optional operation 840, it may be attempted to detect pacing artifacts from at least two of the channels, and render generic pacing values from such artifacts.

Then, according to another, optional operation 844, it may then be attempted to input two sets of generic pacing values rendered, by the operation 840, by the pacing signal detection functionality from two candidate ones of the channels.

According to another operation 845, it can be inquired whether or not the operation 844 was successful or not. If not successful, the reason may be that the pacemaker 87 is not emitting any pulses or it is, but in neither channel do they result in a detectible artifact. As such, if not successful, then the execution may return to the operation 810 for sensing another portion of the ECG signal. Or, instead, for a number of times, the execution may return to the operation 840 for trying different combinations of candidate channels.

If, however, at the operation 845, it is answered that the operation 844 was successful then, execution may proceed to operation 857. In particular, responsive to the attempting inputting of the two sets of the generic pacing values being successful, it may be determine that the set of the generic pacing values that correspond to a first one of the two candidate channels meet a preference criterion better than the set of the generic pacing values that correspond to a second one of the two candidate channels and, in response to so determining, identifying the first one of the two candidate channels as the preferential one of the channels. The operation 857 may be performed in ways similar to the operation 957.

According to another, optional operation 859, the preferential channel may be established. The operation 859 may be performed in ways similar to the operation 959.

Identifying a preferential or preferred channel is now described in more detail. As already written above, one or more preference criteria may be used. One of the channels may be identified as the preferential one of the channels because it results in pacing values that meet a preference criterion better than pacing values of another one of the channels.

Figure 10:
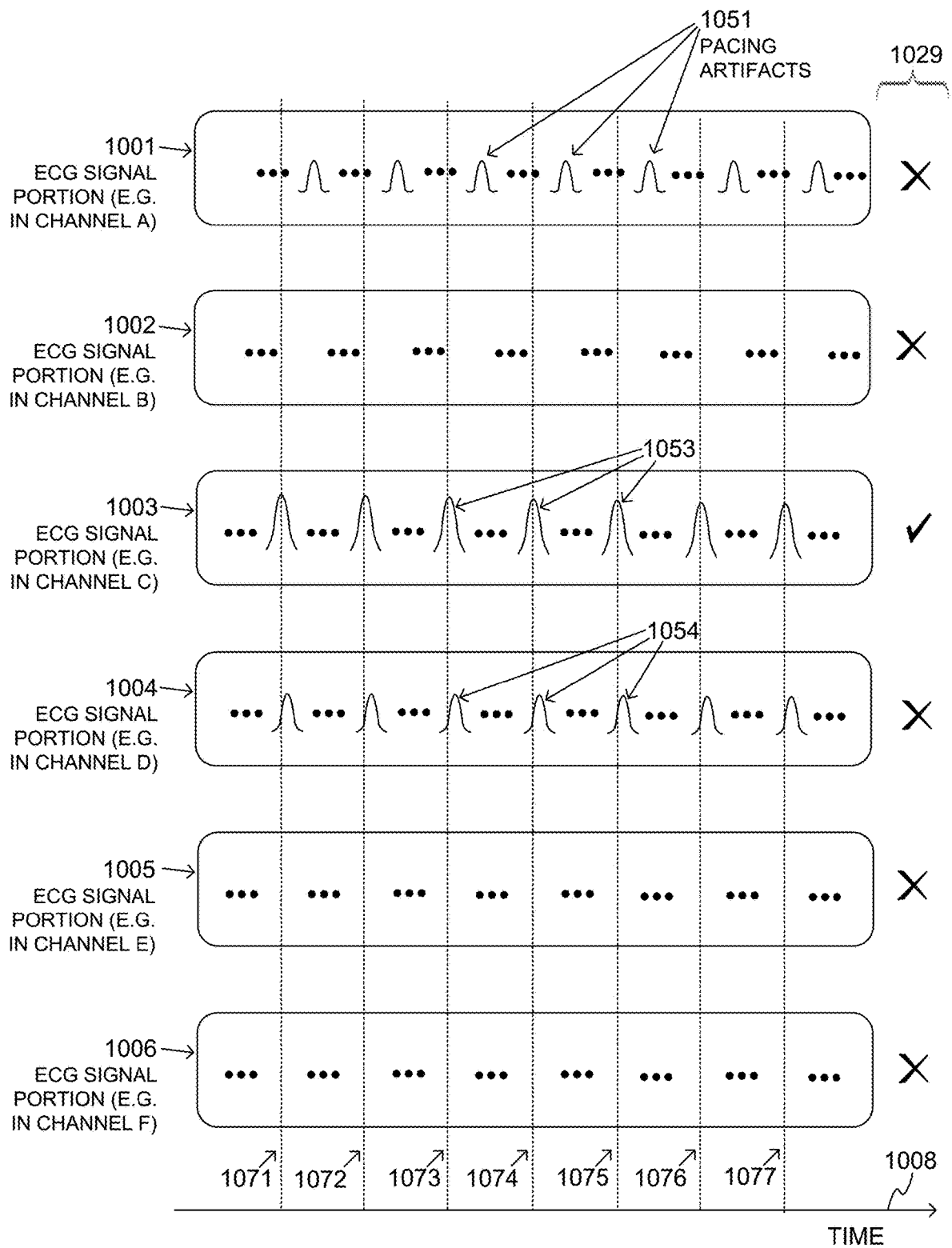
FIG. 10 shows time diagrams of salient aspects of sample ECG signal portions from multiple channels, such as the channels of FIG. 4, some of which have pacing artifacts, for discussing preference criteria in identifying a preferential or preferred channel according to embodiments.

FIG. 10 shows time diagrams of salient aspects of sample ECG signal portions from multiple channels, such as the channels of FIG. 4, some of which have pacing artifacts, for discussing how a channel selection may be performed according to one or more preference criteria according to embodiments. One or more of these preference criteria may be used. Not every one of these preference criteria needs to be used every time.

In FIG. 10, a horizontal time axis 1008 for comparing six concurrent ECG signal portions 1001, 1002, 1003, 1004, 1005, 1006. These could be, for example the signals in channels A, B, C, D, E, F of the WCD system of FIG. 4.

The ECG signal portions 1001, 1002, 1003, 1004, 1005, 1006 will be compared for their pacing artifacts to determine the preferred or preferential channel. Strictly speaking the pacing artifacts can be detected from at least the raw ECG signal, even though in most embodiments they are detected and processed separately from the raw ECG signal. In this diagram, the pacing artifacts are shown as embedded in their respective raw ECG signals as actual artifacts in the waveform, but that is done only for conceptual purposes, and after having explained that they are, in fact much narrower and of lesser duration that features of the ECG signal. As seen in FIG. 10, these ECG signal portions 1001, 1002, 1003, 1004, 1005, 1006 are not necessarily those that are processed to make the shock/no shock decisions; rather, what is processed is often the ECG signal with just the pacing values, for instance just the pacing markers.

In FIG. 10 these ECG signal portions 1001, 1002, 1003, 1004, 1005, 1006 are shown as concurrent, as is preferred. However, for performing the comparison, it is not necessary to compare ECG signal portions that are concurrent. And, even when concurrent, these signals will be compared in pairs, for determining whether a preference criterion is met.

As the comparison of this example proceeds, indicia 1029 will be assigned to each of the ECG signal portions 1001, 1002, 1003, 1004, 1005, 1006 according to their desirability. These indicia 1029 can be an "X" for a channel that is not wanted, until reaching a checkmark for the preferential channel.

For each of these channels, the first question is whether pacing artifacts are detected at all. None are detected in ECG signal portions 1002, 1005 and 1006, all of which therefore are assigned an "X" as their indicia 1029, and therefore are removed from consideration. It should be noted that, given that pacing artifacts are detected in at least another channel, there are also pacing artifacts in the ECG signal portions 1002, 1005 and 1006, but likely these pacing artifacts are too weak to be detected, from conditions like noise, placement of the electrodes relative to the position of the implanted heart pacing device 87, and so on.

In the remaining three channels, pacing artifacts 1051 are detected in ECG signal portion 1001, pacing artifacts 1053 are detected in ECG signal portion 1003, and pacing artifacts 1054 are detected in ECG signal portion 1004. In this example, all these pacing artifacts are of the same frequency, and a potentially valid frequency. In some instances, they could be of a not valid frequency; for instance, a pacemaker would not be pacing at 200 bpm.

For choosing the preferential channel, a number of possible preference criteria may be used. One of them is a regularity criterion about the time period or frequency mentioned below.

Other embodiments are possible. For instance, one preference criterion may be the amplitude of the detected pacing artifacts. The larger the better. By inspection, the pacing artifacts 1053 are taller than the pacing artifacts 1051, 1054.

It should be remembered that the processing may be performed either at the signal level with voltages, or at the numerical level with values. Accordingly, between two candidate channels, a first one of the two candidate channels may be chosen as the preferential channel when the preference criterion includes that the pacing artifacts from the first one of the two candidate channels have larger amplitudes than the pacing artifacts from the second one of the two candidate channels. Or, again, between two candidate channels, a first one of the two candidate channels may be chosen as the preferential channel when the preference criterion includes that the pacing values rendered from the first one of the two candidate channels are larger than the pacing values rendered from the second one of the two candidate channels.

For choosing the preferential channel, another preference criterion may include that the pacing artifacts from the first one of the two candidate channels occur within a threshold time difference from the pacing artifacts from the second one of the two candidate channels. In other words, the detection of pacing artifacts is trusted more when the pacing artifacts are detected close—in time—to the pacing artifacts in another channel. For implementing this preference criterion, of course, it is preferred for the compared ECG signal portions to be concurrent.

First it can be observed that, in the detailed example of FIG. 10, the remaining detected pacing artifacts 1051, 1053, 1054 are offset from each other, in time. A small amount of this offset can be expected, considering the different locations of the vectors that have these channels. A large amount of this offset, however, can be suspect as to the quality of detection of the pacing artifacts.

To judge how close in time are all the remaining detected pacing artifacts 1051, 1053, 1054, vertical time lines 1071, 1072, 1073, 1074, 1075, 1076, 1077 are drawn at the peaks of one of these sets. In this case, these vertical time lines are drawn through the peaks of the detected pacing artifacts 1053, because they are the ones that are already taller and therefore come from a channel that is already a good candidate for being the preferential channel. It will be observed that the peaks of the detected pacing artifacts 1054 are very close—in time—to those of the detected pacing artifacts 1053, which further validates both sets. The detected pacing artifacts 1051, however, seem to be off by themselves, which can make their detection can be suspect.

In the example of FIG. 10 the threshold time difference is not shown to not further complicate the drawing. In practical matters, the threshold time difference can be defined as a percentage of the time period between the detected peaks. A time period of less than 25% should be adequate for this validation.

As such, in the example of FIG. 10, the ECG signal portions 1001 and 1004, are also assigned an "X" as their indicia 1029, while the channel C in which the ECG signal portion 1003 is detected is assigned a checkmark. Channel C has been identified as the preferential channel, and may be established and so on.

For the descriptions in the remainder of the document, it should be remembered that a WCD system according to some embodiments may have just two electrodes, or sensors, for sensing the ECG, in which case there is only one vector and only one channel. A WCD system according to other embodiments may have more than one such sensors, for instance as indicated in the example of FIG. 3.

In embodiments, an ECG signal portion may be sensed, from at least one sensor, for determining whether or not an alert condition is met, regardless of how many sensors are available sensing ECG signals. In some embodiments, as indicated in FIG. 4, a plurality of additional sensors may be included which, together with a sensor for the ECG signal, pairwise define distinct vectors. In such embodiments, the sensors can be configured to sense respective electrocardiogram (ECG) signals of the ambulatory patient along respective channels for the vectors. A preferential one of the channels may have been previously identified based on the successfully inputted pacing values. The preferential channel may have been defined by a pair of the sensor and one of the additional sensors, and the ECG signal portion can be sensed from the preferential channel.

A pacing signal may or may not cause capture. Capture is when, in response to the pacing signal, the heart responds by the myocardium contracting. Loss of capture is when the heart does not respond.

In embodiments, one or more paced QRS complexes are identified from the pacing artifacts and/or their corresponding pacing values, which may have been rendered in terms of pacing markers, and so on. Examples are now described.

Figure 11:
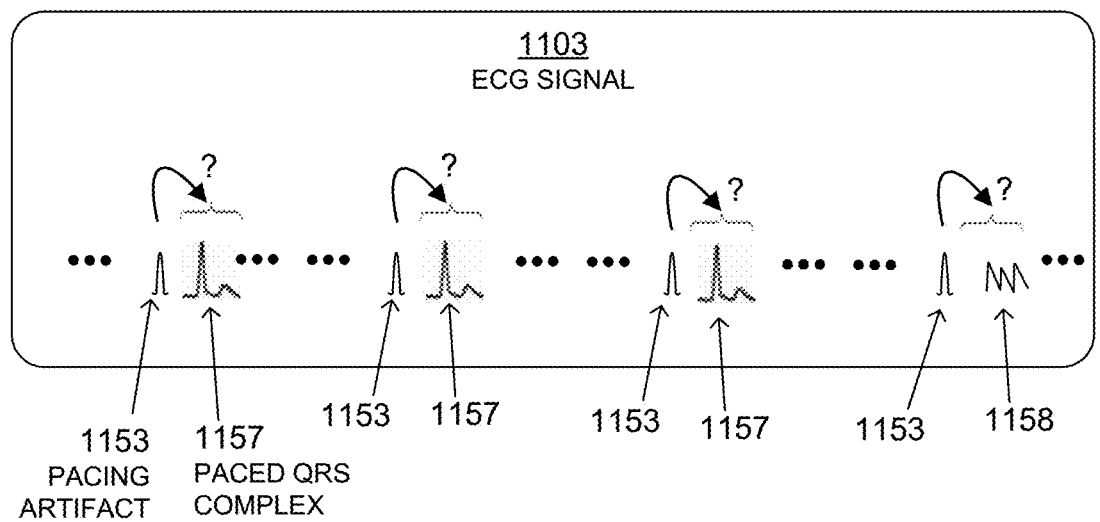
FIG. 11 is a time diagram of sample aspects in a portion of an ECG signal, where detected pacing artifacts are further used to identify candidate paced QRS complexes according to embodiments.

FIG. 11 is a time diagram of sample aspects in a portion of an ECG signal 1103, which could be as the previously described ECG signals. According to embodiments, pacing artifacts 1153 have been detected in the ECG signal portion 1103. Detection can be as described above. Formally, a sample waveform shape is shown for these pacing artifacts 1153 as standalone, after having removed the underlying ECG signal. In reality, in some coarse time resolutions the pacing artifacts appear substantially as spikes superimposed on the ECG signal.

In some embodiments, the detected pacing artifacts 1153 are further used to identify candidate paced QRS complexes. The identification is looking, questioningly, at the candidate waveforms following the detected pacing artifacts 1153. As can be seen, of the candidate waveforms, the waveforms 1157 are paced QRS complexes, while the waveform 1158 is not, reflecting that capture has been lost. The ECG signal 1103 has other features which, however, are represented in FIG. 11 with a dot-dot-dot so as not to unnecessarily clutter the drawing.

In some embodiments, a baseline paced QRS complex may be established, and even be stored in the memory. The baseline paced QRS complex may be established from one or more of the paced QRS complexes, identified at different times. In some embodiments, at least three paced QRS complexes are identified, and the baseline paced QRS complex is established by averaging at least two of the at least three paced QRS complexes. An example is now described.

Figure 12:
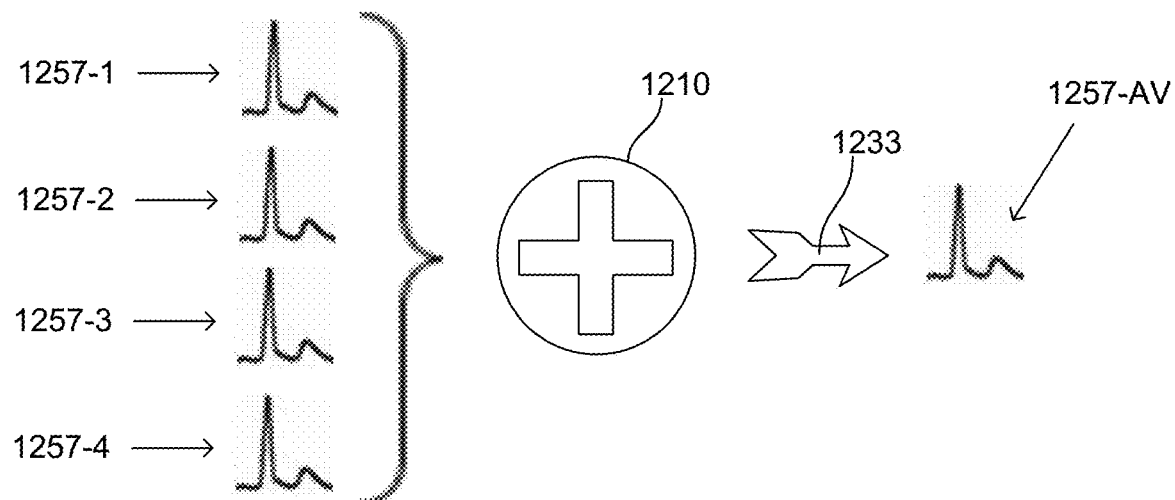
FIG. 12 is a conceptual diagram for showing how paced QRS complexes, such as those identified in FIG. 11, can be averaged according to embodiments.

FIG. 12 is a conceptual diagram for showing four paced QRS complexes 1257-1, 1257-2, 1257-3, 1257-4, which can be identified as described for FIG. 11. These four paced QRS complexes can be superimposed, and added and averaged by an operation 1210. The operation 1210, according to an arrow 1233, yields the average waveform 1257-AV. It should be remembered that, in embodiments, the operation of FIG. 12 may be applied to identified QRS complexes, paced or not paced, for establishing a baseline or for detecting the state of the patient.

Figure 13:
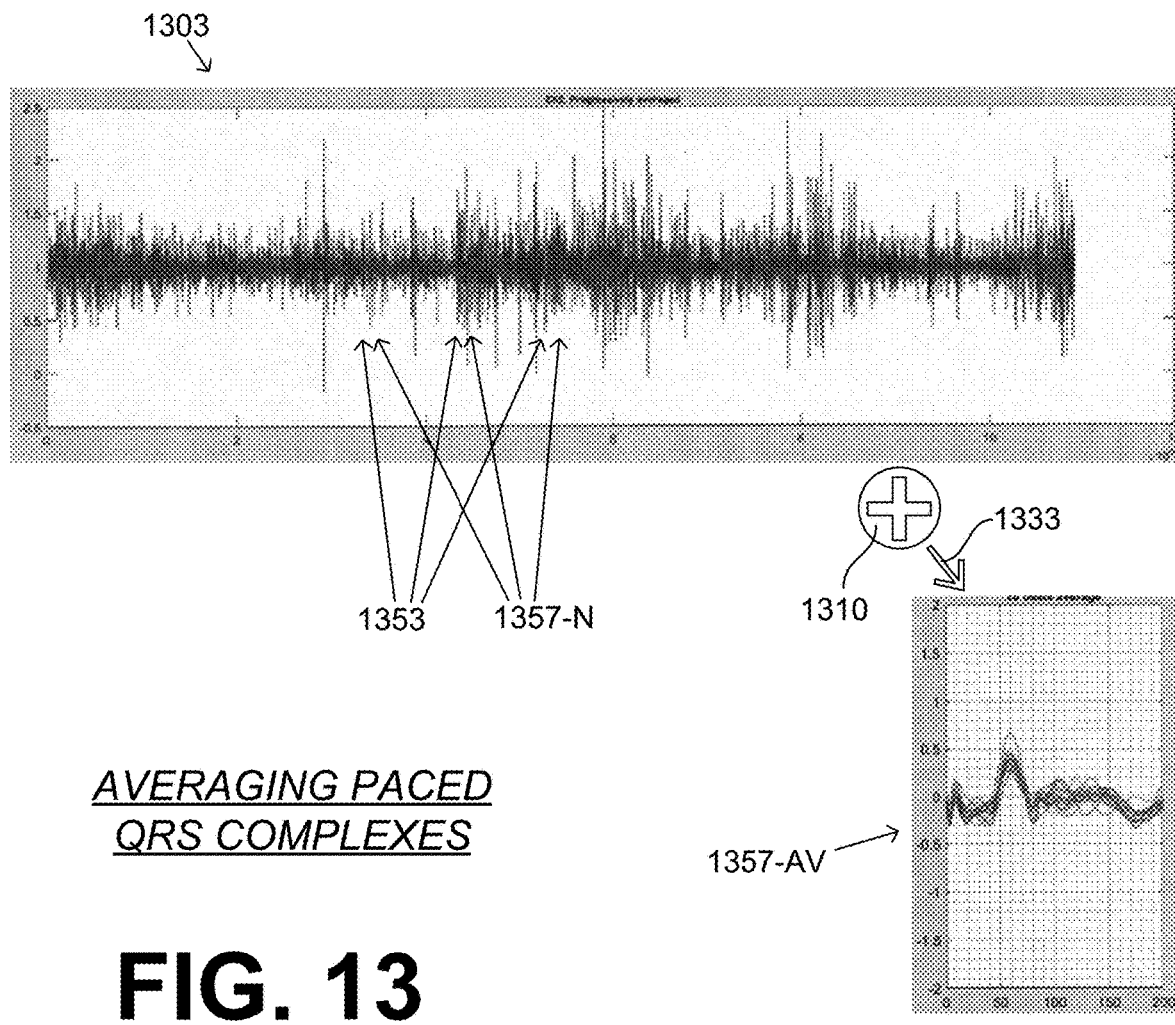
FIG. 13 shows two diagrams, in which the first diagram shows an ECG signal portion that is heavily corrupted by noise, and yet according to embodiments paced QRS complexes can be identified in it and then averaged, to produce a recognizable average paced QRS complex that is shown in the second diagram.

FIG. 13 shows two diagrams. The top diagram is an ECG signal portion 1303 that is heavily corrupted by noise. It will be appreciated that this type of noise was not shown in earlier-described diagrams of the ECG signal portions. In embodiments, the WCD system is capable of detecting pacing signals 1353 and, from those, detect paced QRS complexes 1357-N, as was described with reference to FIG. 11. Of course, N here would be 1, 2, 3, . . . and so on. Moreover, an averaging operation 1310 similar to the operation 1210 would yield, per an arrow 1333, an averaged paced QRS complex 1357-AV in the second diagram. It will be appreciated that the various individual identified paced QRS complexes 1357-N largely overlap.

In some embodiments, a newly identified paced QRS complex is compared to a previously established baseline paced QRS complex, for determining whether a shock criterion is met, and/or whether the patient's condition is worsening such that it causes a shock criterion to be met subsequently. An advantage can be that paced QRS complexes might not be confused for noise in certain circumstances, thereby improving the performance of the system. Plus, determining the severity of an event can become more accurate when the patient has an implanted pacemakers that is independently emitting pacing signals. An example is now described.

Figure 14:
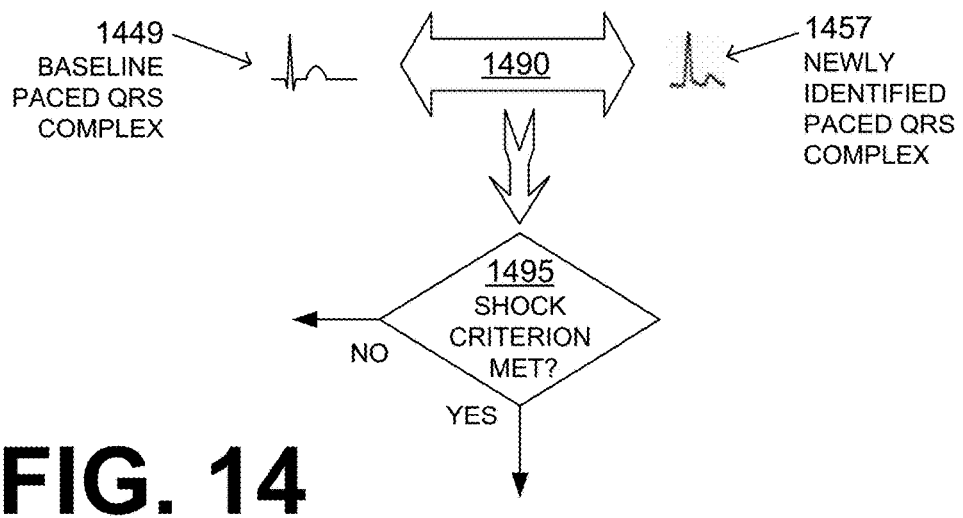
FIG. 14 is a conceptual diagram for showing that a determination of whether or not a sample shock criterion is met can be made according to embodiments by comparing a newly identified paced QRS complex to a previously stored baseline paced QRS complex.

FIG. 14 is a conceptual diagram showing a baseline paced QRS complex 1449, which has been established according to embodiments. FIG. 14 also shows a newly-identified paced QRS complex 1457. According to an arrow 1490, it is determined from the baseline paced QRS complex 1449 and the paced QRS complex 1457 whether or not a shock criterion is met. According to another operation 1495, it can be inquired whether or not the shock criterion was met, and act accordingly.

Figure 15:
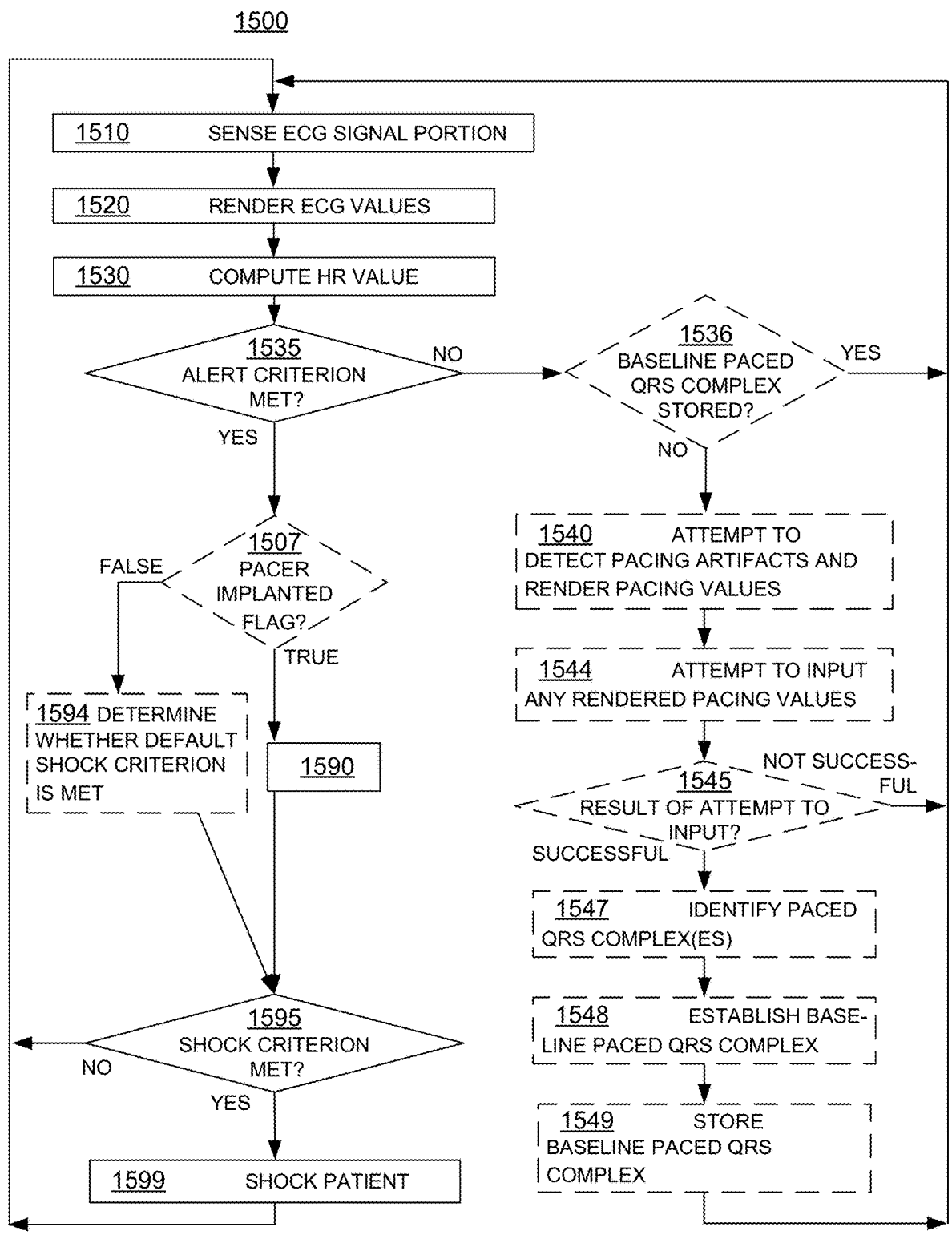
FIG. 15 is a flowchart for illustrating sample methods according to embodiments.

FIG. 15 shows a flowchart 1500 for describing methods according to embodiments. According to an operation 1510, an ECG signal portion may be sensed, for example by sensors as described above. Of course, a plurality of sensors may also be used, and so on.

According to another operation 1520, ECG values for the ECG signal portion can be rendered. This can be performed as described above, for example by a measurement circuit.

According to another operation 1530, a heart rate (HR) value may be computed from the ECG values. This can be performed as described above.

According to another operation 1535, it may be determined, from at least the HR value, whether or not an alert criterion is met. This can be performed as described above.

If, at the operation 1535, the answer is yes then, according to an optional next operation 1507, it may be determined what is the value of the pacer implanted flag, assuming the flag is provided and has been set to true or false. This can be performed similarly with what is written for the operation 807.

If, at the operation 1507, the answer is true, it means that the WCD system knows that this patient has an implanted heart pacing device, which could be emitting pacing signals. Then a group 1590 of operations can be performed, which are described later in this document with reference to FIG. 16. These operations of group 1590 end up with determining whether or not a shock criterion is met. Then execution proceeds to an operation 1595.

If, at the operation 1507, the answer is false, it means that the WCD system knows that this patient does not have an implanted heart pacing device in the first place. According to a next operation 1594, it may be determined whether or not a default shock criterion is met, one that does not take into account the outputs of the pacing signal detection functionality 221, 521. Then execution again proceeds to the operation 1595.

According to the operation 1595, it may be inquired whether or not a shock criterion is met. Of course, which shock criterion will depend on which path the operation 1595 was arrived from. If from operation 1594, then the shock criterion is the default shock criterion of operation 1594. If from group 1590, then accordingly.

If, at the operation 1595, it is learned that the applicable shock criterion is met then, according to another operation 1599, the stored electrical charge can be caused to be discharged via the electrodes through the ambulatory patient 82 so as to deliver the shock 111 to the ambulatory patient 82. However, responsive to the applicable shock criterion not being met, no electrical charge is caused to be thus discharged responsive to this ECG signal portion. After that, the execution may again return to the operation 1510 for sensing another portion of the ECG signal, and so on with monitoring the patient 82.

In particular, resulting from operation 1507, the processor 230 can be further configured to attempt the inputting of any of the pacing values rendered from the pacing signal detection functionality 221, 521, only responsive to the pacer implanted flag having a value of true, but, responsive to the pacer implanted flag having a value of false, not so attempt and instead determine whether or not the default shock criterion is met and responsive to the default shock criterion being met, cause at least some of the stored electrical charge to be discharged via the electrode through the ambulatory patient so as to deliver a shock to the ambulatory patient, but not cause any electrical charge to be thus discharged responsive to the default shock criterion not being met.

Before completing the description of the remaining operations shown in FIG. 15, the group 1590 of operations is now described in more detail with reference to FIG. 16.

Figure 16:
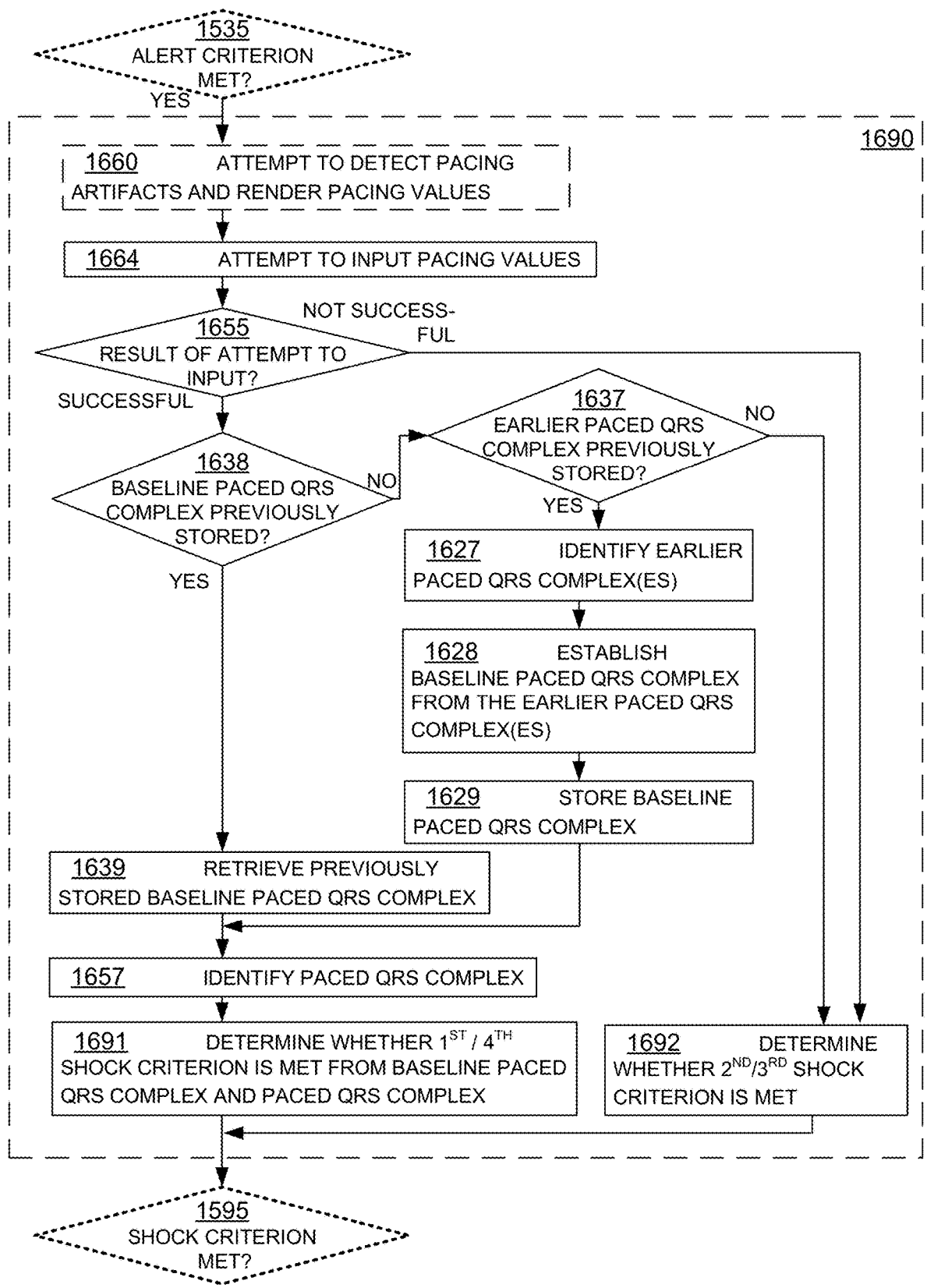
FIG. 16 is a flowchart for illustrating sample methods for performing a group of operations of the flowchart of FIG. 15 according to embodiments.

FIG. 16 shows a group 1690 of operations that can be embodiments for the group 1590 of operations. In addition, and for better reference, FIG. 16 repeats in dotted lines the above-described operations 1535 and 1595 of FIG. 15.

According to another, optional operation 1660, it may be attempted to detect pacing artifacts, and render preferential pacing values from such artifacts. These may be detected in any channel, and be performed as described above, for example by the pacing signal detection functionality 221, 521.

According to another operation 1664, it may then be attempted to input any such pacing values rendered from the pacing signal detection functionality. This can be performed similarly with operation 555 of FIG. 5.

According to another operation 1665, it can be inquired whether or not the operation 1664 was successful or not. If successful then, according to an optional operation 1638, it can be determined whether or not a baseline paced QRS complex has been previously stored in the memory. At the operation 1638 the default answer is no meaning that, in embodiments where the operation 1638 is not performed, the execution follows the direction of the answer being no, for reasons analogous to those given above for similar operations.

And if, at the operation 1638, the answer is yes then, according to an optional operation 1639, the baseline paced QRS complex can be retrieved from the memory. Then according to another operation 1657, a paced QRS complex can be identified from the pacing values.

Then, according to another operation 1691, it may be determined whether or not a first shock criterion is met from the baseline paced QRS complex and the paced QRS complex. Then execution may proceed to operation 1595 as per the above.

If, however, at the operation 1665, it is answered that the operation 1664 was not successful then, according to another, optional operation 1692, it may be determined without any pacing values whether or not a second shock criterion is met. Again, since no pacing is involved, the second shock criterion can even be as the default criterion of operation 1594. Then execution may proceed to operation 1595 as per the above.

Alternatively, if at the operation 1638 the answer is no, then according to another, optional operation 1637 it may be determined whether or not earlier paced QRS complexes ("beats") have been previously stored, as described below. If not then, according to the optional operation 1692 it can be determined whether or not a third shock criterion is met. The third shock criterion can be the same as the second shock criterion, or different. Here a single operation 1692 is shown for potentially different criteria, namely a second or a third one. This is done here, as in other places in this document, to reduce how busy these drawings are.

If, however, at the operation 1637, the answer is yes, then a baseline paced QRS complex can be established on the fly from earlier ECG signal portions, and then applied to later ECG signal portions, similarly to how it was described for ECG signal 408 in FIG. 4. This can be performed by having the WCD system record earlier ECG signal portions, without processing them. If enough time passes, such as two minutes, then it may discard them.

In such embodiments, the sensor may have previously sensed an earlier ECG signal portion of the ambulatory patient, the measurement circuit may have rendered earlier ECG values for the earlier ECG signal portion, and the pacing signal detection functionality may have detected earlier pacing artifacts included in the earlier ECG signal portion. The earlier pacing artifacts may have occurred at least 10 sec prior to the pacing artifacts, or 25 sec, or 45 sec, or 75 sec, or 12 sec, and so on. The pacing signal detection functionality may have further rendered earlier pacing values from the earlier pacing artifacts.

In embodiments, the baseline paced QRS complex can be established from earlier ECG signal portions as follows: According to another, optional operation 1627, one or more earlier paced QRS complexes may be identified from the earlier pacing values. Then according to another, optional operation 1628, a baseline paced QRS complex may be established from the one or more earlier paced QRS complexes, for example as shown in FIG. 12. According to one more, optional operation 1629, the baseline paced QRS complex may be stored in the memory. This may be valuable, because it was obtained during a stress time, while the alert condition was not met, and so on. Then the operation 1657 and 1691 may be repeated, but operation 1691 may be repeated for a fourth shock criterion. The fourth shock criterion can be the same as the first shock criterion, or not, etc.

Returning to FIG. 15 if, at the operation 1535 it is determined that the alert criterion is not met, then there is likely no cause for alarm. A shock to the patient will not result based on the ECG signal portion that was thus analyzed at the earlier operations of this flowchart. Nevertheless, in some embodiments, the opportunity is used to try to identify, and store and establish, a baseline paced QRS complex for later, in the event that the alert criterion might not be met later.

As such, if at the operation 1535 the answer is no then, according to an operation 1536, it can be optionally inquired whether or not a baseline paced QRS complex has been previously stored in the memory. This may be performed similarly with the operation 1638; in fact, the operation 1536 is optional at least in the same sense as the operation 1638. In other words, at the operation 1536 the default answer is yes meaning, if the operation 1536 is not performed, the execution follows the direction of the answer being yes.

As a caution, operation 1536 may be performed only if the pacer implanted flag has a value of true, else the execution may return to the operation 1510. In other words, the operation 1507 can be repeated immediately prior to operation 1536, except that was not drawn so as not to clutter the drawing.

If at the operation 1536 the answer is yes, then the execution may return to the operation 1510 for sensing another portion of the ECG signal, since a baseline paced QRS complex has already been established.

If, however, at the operation 1536 the answer is no, then the processor can be further configured to establish a baseline paced QRS complex per an operation 1548, and then store the established baseline paced QRS complex in the memory per an operation 1549.

In some embodiments, this is performed by first an operation 1540, where it may be attempted to detect pacing artifacts, and render generic pacing values from such artifacts. Then, by an operation 1544, it may then be attempted to input pacing values rendered by the pacing signal detection functionality. Then, according to another operation 1545, it can be inquired whether or not the operation 1544 was successful or not. If not successful, the reason may be that the pacemaker 87 is not emitting any pulses or it is, but no pacing artifact is detected. As such, if not successful, then the execution may return to the operation 1510 for sensing another portion of the ECG signal.

If, however, at the operation 1545, it is answered that the operation 1544 was successful then, execution may proceed to operation 1547. In particular, responsive to the attempting inputting of the pacing values being successful, one or more paced QRS complexes may be identified from the pacing values. In such embodiments, the baseline paced QRS complex can be established from the identified one or more paced QRS complexes.

As mentioned above, a validation criterion for the pacing artifacts is that they occur at regular time intervals, when taken in sequence. An example is are now described.

Figure 17:
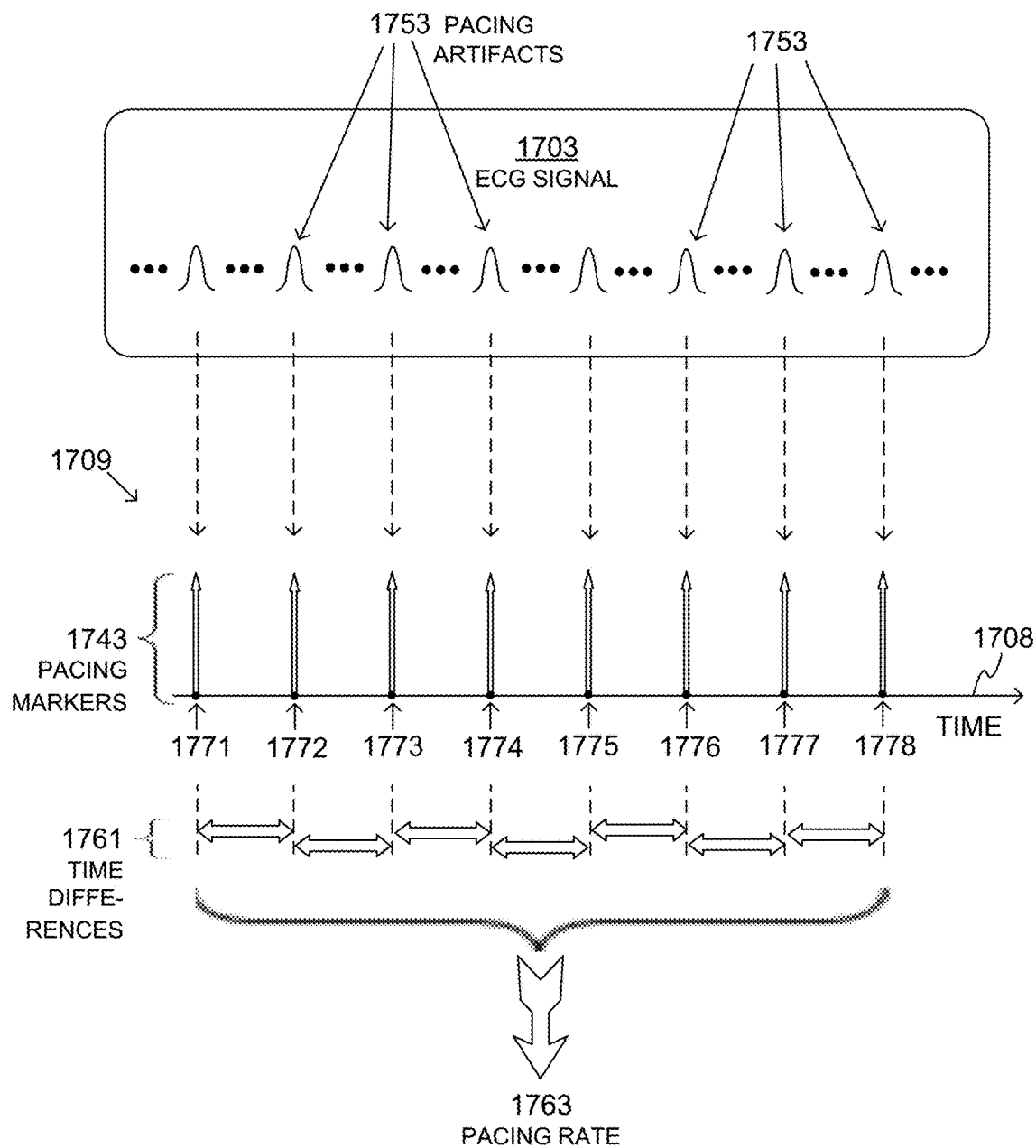
FIG. 17 is a time diagram showing a sample way according to embodiments for extracting a pacing rate of pacing artifacts that are detected in an ECG signal.

FIG. 17 is a time diagram having a horizontal time axis 1708, which is used in a diagram 1709 and also for sample aspects of a portion of an ECG signal 1703. The portion 1703 can be as for previously described ECG signal portions. According to embodiments, pacing artifacts 1753 have been detected in the ECG signal portion 1703. Detection can be as described above. Again, a sample waveform shape is shown for these pacing artifacts 1753 as standalone, after having removed the underlying ECG signal.

In the diagram 1709, pacing markers 1743 are defined for these pacing artifacts 1753, from their pacing values. For instance, each pacing signal marker 1743 can be at the peak of each waveform of each of the artifacts 1753. In some embodiments, times 1771, 1772, 1773, 1774, 1775, 1776, 1777, 1778, are identified for the pacing markers. In such embodiments, time differences 1761 can be measured. The time differences 1761 can be differences of the times 1771, 1772, 1773, 1774, 1775, 1776, 1777, 1778, of successive ones of the pacing markers 1743. In such embodiments, a pacing rate 1763 can be extracted from the time differences 1761. The extracted pacing rate 1763 can be stored, then used again to guess more quickly at a subsequent time whether or not the validation criterion is met, and so on.

In some embodiments, a WCD system may override an internal elevated heart-rate-based alert based on regular pacing signals detected in the patient. Examples are now described.

Figure 18:
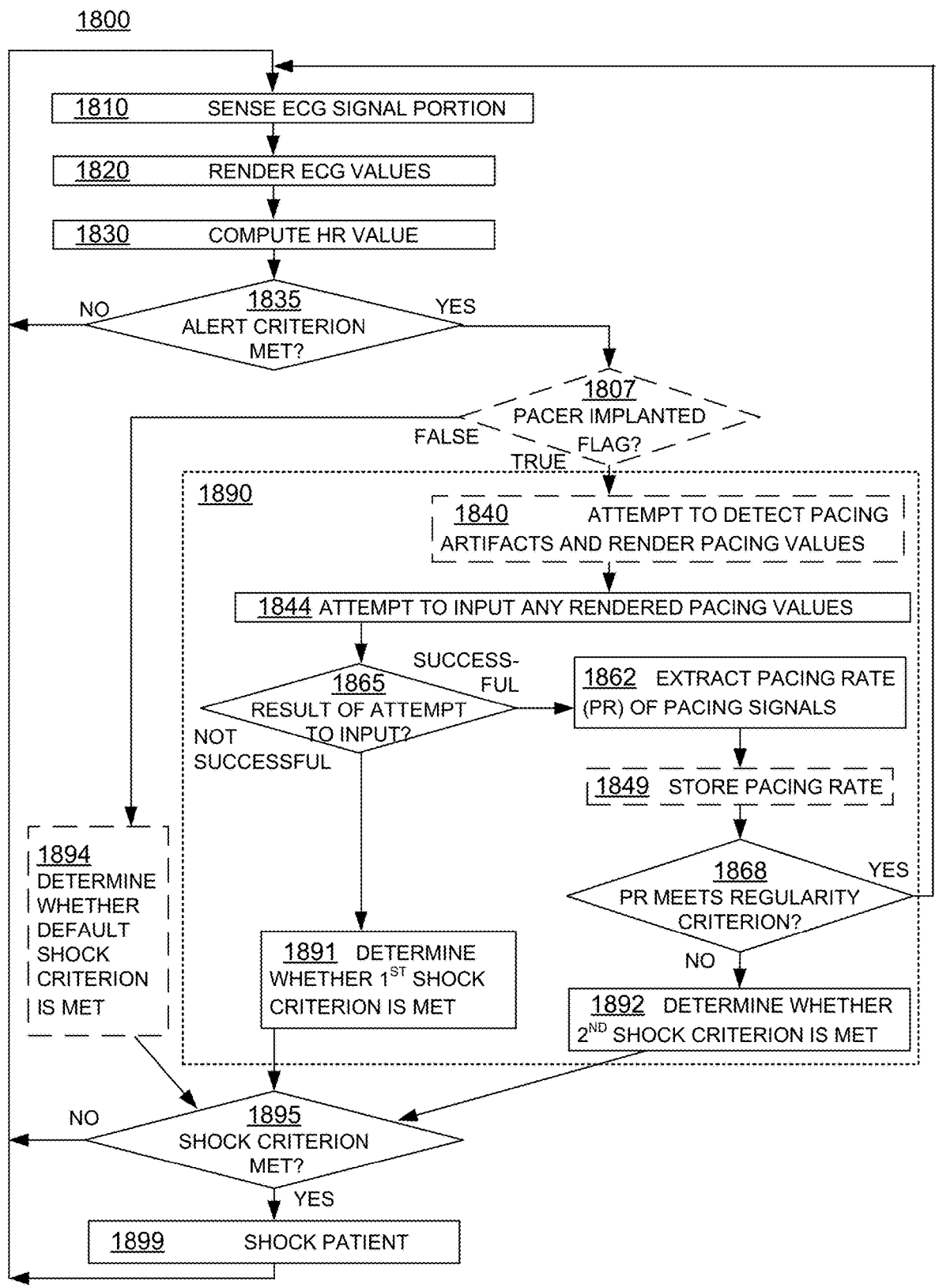
FIG. 18 is a flowchart for illustrating sample methods according to embodiments.

FIG. 18 shows a flowchart 1800 for describing methods according to embodiments. According to an operation 1810, an ECG signal portion may be sensed, for example by sensors as described above. Of course, a plurality of sensors may also be used, and so on.

According to another operation 1820, ECG values for the ECG signal portion can be rendered. This can be performed as described above, for example by a measurement circuit.

According to another operation 1830, a heart rate (HR) value may be computed from the ECG values. This can be performed as described above.

According to another operation 1835, it may be determined, from at least the HR value, whether or not an alert criterion is met. This can be performed as described above. In embodiments, this is an internal alert criterion.

If, at the operation 1835 the answer is no, then execution may return to operation 1810, for sampling another ECG signal portion, and so on with monitoring the patient 82. Accordingly, there will be no shocking the patient based on the ECG signal portion that was thus analyzed at the earlier operations of this flowchart.

If, at the operation 1835, the answer is yes then, according to an optional next operation 1807, it may be determined what is the value of the pacer implanted flag, assuming the flag is provided and has been set to true or false. This can be performed similarly with what is written for the operation 807.

If, at the operation 1807, the answer is true, it means that the WCD system knows that this patient has an implanted heart pacing device, which could be emitting pacing signals. Then a group 1890 of operations can be performed. These operations of group 1890 end up with determining whether or not a shock criterion is met. Then execution proceeds to an operation 1895.

If, at the operation 1807, the answer is false, it means that the WCD system knows that this patient does not have an implanted heart pacing device in the first place. According to a next operation 1894, it may be determined whether or not a default shock criterion is met, one that does not take into account the outputs of the pacing signal detection functionality 221, 521. Then execution again proceeds to the operation 1895.

According to the operation 1895, it may be inquired whether or not a shock criterion is met. Of course, which shock criterion will depend on which path the operation 1895 was arrived from. If from operation 1894, then the shock criterion is the default shock criterion of operation 1894. If from group 1890, then accordingly.

If, at the operation 1895, it is learned that the applicable shock criterion is met then, according to another operation 1899, the stored electrical charge can be caused to be discharged via the electrodes through the ambulatory patient 82 so as to deliver the shock 111 to the ambulatory patient 82. However, responsive to the applicable shock criterion not being met, no electrical charge is caused to be thus discharged responsive to this ECG signal portion. After that, the execution may again return to the operation 1810 for sensing another portion of the ECG signal, and so on with monitoring the patient 82.

In particular, resulting from operation 1807, the processor 230 can be further configured to attempt the inputting of any of the pacing values rendered from the pacing signal detection functionality 221, 521 only responsive to the pacer implanted flag having a value of true, but, responsive to the pacer implanted flag having a value of false, not so attempt and instead determine whether or not the default shock criterion is met and responsive to the default shock criterion being met, cause at least some of the stored electrical charge to be discharged via the electrode through the ambulatory patient so as to deliver a shock to the ambulatory patient, but not cause any electrical charge to be thus discharged responsive to the default shock criterion not being met.

The operations of the group 1890 have been groups within the flowchart 1800 only for the ease of this description.

According to another, optional operation 1840, it may be attempted to detect pacing artifacts, and render preferential pacing values from such artifacts. These may be detected in any channel, and be performed as described above, for example by the pacing signal detection functionality 221, 521.

According to another operation 1844, it may then be attempted to input any such pacing values rendered from the pacing signal detection functionality. This can be performed similarly with operation 555 of FIG. 5.

According to another operation 1865, it can be inquired whether or not the operation 1844 was successful or not. If at the operation 1865, it is answered that the operation 1864 was not successful then, according to another, optional operation 1891, it may be determined without any pacing values whether or not a first shock criterion is met. Again, since no pacing is involved, the first shock criterion can even be as the default criterion of the operation 1894. Then execution may proceed to the operation 1895 as per the above.

If at the operation 1865, it is answered that the operation 1864 was successful then, according to another operation 1862, a pacing rate (PR) of the pacing signals can be extracted from the pacing values. For instance, it was shown how to extract such a pacing rate 1763 with reference to FIG. 17. In fact, in some embodiments, according to an additional operation 1849, the extracted pacing rate can be stored in the memory 238.

Then, according to another operation 1868, it can be optionally be determined whether or not the pacing rate meets a regularity criterion. This can be performed in a number of ways. For instance, the pacing rate may meet the regularity criterion if it has a value between 50 beats per minute and 65 beats per minute.

In some embodiments, the regularity criterion can be validated by further confirming that capture has also happened, as was described with reference to FIG. 11. For instance, the processor can be further configured to validate the regularity criterion by further confirming that, based on the pacing values rendered from detected pacing artifacts (1153 in FIG. 11), paced QRS complexes (1157) indeed follow the detected pacing artifacts.

If, at the operation 1868, the answer is no then, according to the optional operation 1892 it can be determined whether or not a second shock criterion is met. The second shock criterion can be the same as the first shock criterion, because both involve no pacing. Then execution may proceed to operation 1895 as per the above.

If, however, at the operation 1868, the answer is yes, then execution may return to operation 1810 and a false positive has been avoided. The patient need not even be notified. The operation 1868 is thus analogous to operation 570 of FIG. 5. In other words, the processor has overridden the internal alert criterion being met at the operation 1835, by detecting pacing artifacts and rendering pacing values per the operation 1840, inputting the pacing values per the operations

1844 and 1865, extracting the pacing rate per the operation 1862 and determining that the patient is actually OK from the operation 1868.

In some embodiments, a WCD system may override an internal elevated heart-rate-based alert, based on an updated heart rate from detected paced QRS complexes. Examples are now described.

Figure 19:
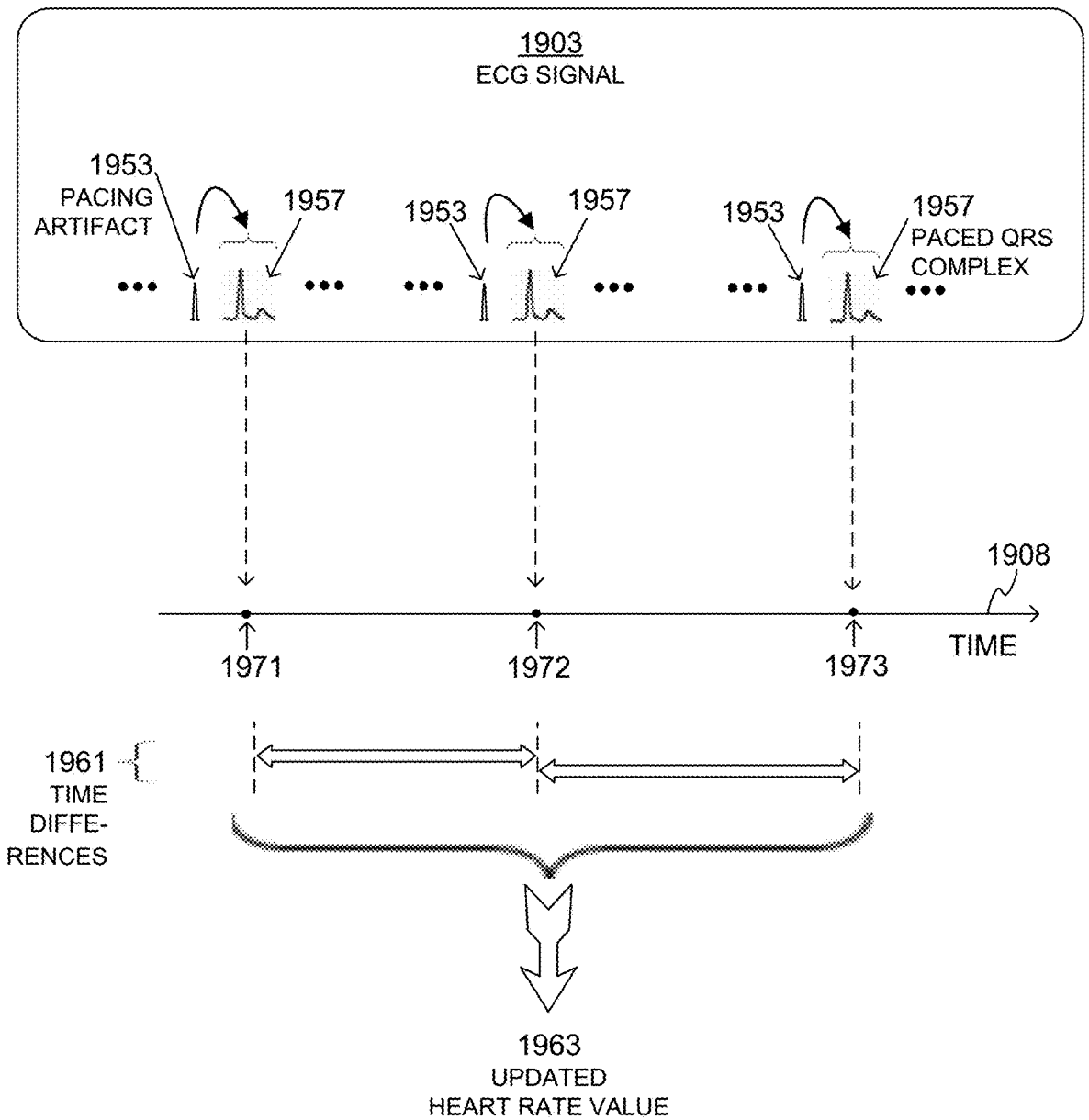
FIG. 19 is a time diagram showing a sample way according to embodiments for computing an updated heart rate from paced QRS complexes that are detected in an ECG signal.

FIG. 19 is a time diagram having a horizontal time axis 1908, which is used for sample aspects of a portion of an ECG signal 1903. The portion 1903 can be as for previously described ECG signal portions. According to embodiments, pacing artifacts 1953 have been detected in the ECG signal portion 1903. Detection can be as described above. Again, a sample waveform shape is shown for these pacing artifacts 1953 as standalone, after having removed the underlying ECG signal.

Moreover, paced QRS complexes 1957 have been identified, for instance as described above. In some embodiments, occurrence times 1971, 1972, 1973, are identified for the identified paced QRS complexes. In such embodiments, time differences 1961 can be measured. The time differences 1961 can be differences of the occurrence times 1971, 1972, 1973, of successive ones of the paced QRS complexes 1957. In such embodiments, an updated heart rate 1963 can be computed from the time differences 1961. The computed updated heart rate 1963 can further be stored in the memory, and so on.

FIG. 20 shows a flowchart 2000 for describing methods according to embodiments. According to an operation 2010, an ECG signal portion may be sensed, for example by sensors as described above. Of course, a plurality of sensors may also be used, and so on.

According to another operation 2020, ECG values for the ECG signal portion can be rendered. This can be performed as described above, for example by a measurement circuit.

According to another operation 2030, a heart rate (HR) value may be computed from the ECG values. This can be performed as described above.

According to another operation 2035, it may be determined, from at least the HR value, whether or not an alert criterion is met. This can be performed as described above. In embodiments, this is an internal alert criterion. It is also an early alert criterion, which may be the same or different as an updated alert criterion described later.

If, at the operation 2035 the answer is no, then execution may return to operation 2010, for sampling another ECG signal portion, and so on with monitoring the patient 82. Accordingly, there will be no shocking the patient based on the ECG signal portion that was thus analyzed at the earlier operations of this flowchart.

If, at the operation 2035, the answer is yes then, according to an optional next operation 2007, it may be determined what is the value of the pacer implanted flag, assuming the flag is provided and has been set to true or false. This can be performed similarly with what is written for the operation 807.

If, at the operation 2007, the answer is true, it means that the WCD system knows that this patient has an implanted heart pacing device, which could be emitting pacing signals. Then a group 2090 of operations can be performed. These operations of group 2090 end up with determining whether or not a shock criterion is met. Then execution proceeds to an operation 2095.

If, at the operation 2007, the answer is false, it means that the WCD system knows that this patient does not have an implanted heart pacing device in the first place. According to a next operation 2094, it may be determined whether or not a default shock criterion is met, one that does not take into account the outputs of the pacing signal detection functionality 221, 521. Then execution again proceeds to the operation 2095.

According to the operation 2095, it may be inquired whether or not a shock criterion is met. Of course, which shock criterion will depend on which path the operation 2095 was arrived from. If from operation 2094, then the shock criterion is the default shock criterion of operation 2094. If from group 2090, then accordingly.

If, at the operation 2095, it is learned that the applicable shock criterion is met then, according to another operation 2099, the stored electrical charge can be caused to be discharged via the electrodes through the ambulatory patient 82 so as to deliver the shock 111 to the ambulatory patient 82. However, responsive to the applicable shock criterion not being met, no electrical charge is caused to be thus discharged responsive to this ECG signal portion. After that, the execution may again return to the operation 2010 for sensing another portion of the ECG signal, and so on with monitoring the patient 82.

In particular, resulting from operation 2007, the processor 230 can be further configured to attempt the inputting of any of the pacing values rendered from the pacing signal detection functionality 221, 521 only responsive to the pacer implanted flag having a value of true, but, responsive to the pacer implanted flag having a value of false, not so attempt and instead determine whether or not the default shock criterion is met and responsive to the default shock criterion being met, cause at least some of the stored electrical charge to be discharged via the electrode through the ambulatory patient so as to deliver a shock to the ambulatory patient, but not cause any electrical charge to be thus discharged responsive to the default shock criterion not being met.

The operations of the group 2090 have been groups within the flowchart 2000 only for the ease of this description.

According to another, optional operation 2040, it may be attempted to detect pacing artifacts, and render preferential pacing values from such artifacts. These may be detected in any channel, and be performed as described above, for example by the pacing signal detection functionality 221, 521.

According to another operation 2044, it may then be attempted to input any such pacing values rendered from the pacing signal detection functionality. This can be performed similarly with operation 555 of FIG. 5.

According to another operation 2065, it can be inquired whether or not the operation 2044 was successful or not. If at the operation 2065, it is answered that the operation 2064 was not successful then, according to another, optional operation 2091, it may be determined without any pacing values whether or not a first shock criterion is met. Again, since no pacing is involved, the first shock criterion can even be as the default criterion of the operation 2094. Then execution may proceed to the operation 2095 as per the above.

If at the operation 2065, it is answered that the operation 2064 was successful then, according to another operation 2072, paced QRS complexes may be identified by referring the pacing values to the rendered ECG values, as described above, and also with reference to FIG. 19. Then according to another operation 2073, an updated heart rate (HR) value may be computed from the identified paced QRS complexes. For instance, it was shown how to compute such an updated heart rate value 1963 with reference to FIG. 19. In fact, in some embodiments, the computed updated heart rate value can be stored in the memory 238.

Then, according to another operation 2075, it can be optionally be determined, from at least the updated HR value, whether or not an updated alert criterion is met. This can be performed in a number of ways. For instance, the updated alert criterion can be the same as the alert criterion of the operation 2035. It is just now that the determination of operation 2075 is being performed with the identified paced QRS complexes.

If, at the operation 2075, the answer is yes then, according to the optional operation 2092 it can be determined whether or not a second shock criterion is met. The second shock criterion can optionally be the same as the first shock criterion. Then execution may proceed to operation 2095 as per the above.

If, however, at the operation 2075, the answer is no, then execution may return to operation 2010 and a false positive has been avoided. The patient need not even be notified. The operation 2075 is thus analogous to operation 570 of FIG. 5. In other words, the processor has overridden the early internal alert criterion being met at the operation 2035, by detecting pacing artifacts and rendering pacing values per the operation 2040, inputting the pacing values per the operations 2044 and 2065, computing the updated heart rate value per the operation 2073 and determining that the patient is actually OK from the operation 2075.

In some embodiments, a WCD system may capture a paced QRS complex while the patient could be in a crisis, and compare it to subsequent paced QRS complex. Examples are now described.

FIG. 21 shows a flowchart 2100 for describing methods according to embodiments. According to an operation 2110, an ECG signal portion may be sensed, for example by sensors as described above. Of course, a plurality of sensors may also be used, and so on.

According to another operation 2120, ECG values for the ECG signal portion can be rendered. This can be performed as described above, for example by a measurement circuit.

According to another operation 2130, a heart rate (HR) value may be computed from the ECG values. This can be performed as described above.

According to another operation 2135, it may be determined, from at least the HR value, whether or not an alert criterion is met. This can be performed as described above. In embodiments, this is an internal alert criterion.

If, at the operation 2135 the answer is no, then execution may return to operation 2110, for sampling another ECG signal portion, and so on with monitoring the patient 82. Accordingly, there will be no shocking the patient based on the ECG signal portion that was thus analyzed at the earlier operations of this flowchart.

If, at the operation 2135, the answer is yes then, according to an optional next operation 2107, it may be determined what is the value of the pacer implanted flag, assuming the flag is provided and has been set to true or false. This can be performed similarly with what is written for the operation 807.

If, at the operation 2107, the answer is true, it means that the WCD system knows that this patient has an implanted heart pacing device, which could be emitting pacing signals. Then a group 2190 of operations can be performed. These operations of group 2190 end up with determining whether or not a shock criterion is met. Then execution proceeds to an operation 2195.

If, at the operation 2107, the answer is false, it means that the WCD system knows that this patient does not have an implanted heart pacing device in the first place. According to a next operation 2194, it may be determined whether or not a default shock criterion is met, one that does not take into account the outputs of the pacing signal detection functionality 221, 521. Then execution again proceeds to the operation 2195.

According to the operation 2195, it may be inquired whether or not a shock criterion is met. Of course, which shock criterion will depend on which path the operation 2195 was arrived from. If from operation 2194, then the shock criterion is the default shock criterion of operation 2194. If from group 2190, then accordingly.

If, at the operation 2195, it is learned that the applicable shock criterion is met then, according to another operation 2199, the stored electrical charge can be caused to be discharged via the electrodes through the ambulatory patient 82 so as to deliver the shock 111 to the ambulatory patient 82. However, responsive to the applicable shock criterion not being met, no electrical charge is caused to be thus discharged responsive to this ECG signal portion. After that, the execution may again return to the operation 2110 for sensing another portion of the ECG signal, and so on with monitoring the patient 82.

In particular, resulting from operation 2107, the processor 230 can be further configured to attempt the inputting of any of the pacing values rendered from the pacing signal detection functionality 221, 521 only responsive to the pacer implanted flag having a value of true, but, responsive to the pacer implanted flag having a value of false, not so attempt and instead determine whether or not the default shock criterion is met and responsive to the default shock criterion being met, cause at least some of the stored electrical charge to be discharged via the electrode through the ambulatory patient so as to deliver a shock to the ambulatory patient, but not cause any electrical charge to be thus discharged responsive to the default shock criterion not being met.

The operations of the group 2190 have been groups within the flowchart 2100 only for the ease of this description.

According to another, optional operation 2140, it may be attempted to detect pacing artifacts, and render preferential pacing values from such artifacts. These may be detected in any channel, and be performed as described above, for example by the pacing signal detection functionality 221, 521.

According to another operation 2144, it may then be attempted to input any such pacing values rendered from the pacing signal detection functionality. This can be performed similarly with operation 555 of FIG. 5.

According to another operation 2165, it can be inquired whether or not the operation 2144 was successful or not. If at the operation 2165, it is answered that the operation 2144 was not successful then, according to another, optional operation 2191, it may be determined without any pacing values whether or not a first shock criterion is met. Again, since no pacing is involved, the first shock criterion can even be as the default criterion of the operation 2194. Then execution may proceed to the operation 2195 as per the above.

If at the operation 2165, it is answered that the operation 2144 was successful then, according to another operation 2172, an earlier paced QRS complex may be identified by referring the pacing values to the rendered ECG values, as described above, and also with reference to FIG. 19. Here the adjective "earlier" is intended to distinguish from the adjective "later", as referenced to when artifacts occur within one or more successive ECG signal portions. In addition, the earlier paced QRS complex may be further stored in the memory 238.

And, instead of just one earlier paced QRS complex, multiple ones may be assembled and an average may be derived from them as per the above. In particular, the processor can be further configured to identify a plurality of earlier QRS complexes, and in which the early QRS complex is derived as a statistic of the plurality of earlier QRS complexes. A good number for the plurality is four.

Another operation 2173 is optional, and is described as waiting for a delay time. The processor 230 might actually wait for the delay time, or the delay time may be interpreted as time delay in when features of the ECG signal portion, and/or of a subsequent ECG signal portion occur. The delay time may be any suitable time, such as at least 15 sec, 30 sec, 45 sec, 75 sec, 120 sec, and so on. It will be appreciated that, at this time, the alert criterion has been met, which means the patient either is in some incipient crisis, or a false positive could be developing due to noise. The noise could be exacerbated by the presence of pacing signals.

According to another operation 2182, a later paced QRS complex may be identified. The later paced QRS complex occurs after the earlier paced QRS complex by the above-described delay time in the ECG signal portion, or in a subsequent ECG signal portion.

The earlier and later paced QRS complexes may be identified in a single or multiple ECG signal portions. Accordingly, in some embodiments, prior to the operation 2182, optionally the processor can be further configured to attempt to input, per operation 2174 any later pacing values rendered from the pacing signal detection functionality. In such embodiments, it may be inquired at an operation 2175 whether or not the operation 2174 was successful. If that fails, execution may proceed to operation 2191 for a third shock criterion, which can be as the first. But, if at the operation 2175 there is success, then the later paced QRS complex can be identified from the later pacing values at the operation 2182.

And, again, instead of just one later paced QRS complex, multiple ones may be assembled and an average may be derived from them as per the above. In particular, the processor can be further configured to identify a plurality of later QRS complexes, and in which the later QRS complex is identified as a statistic of the plurality of earlier QRS complexes.

Then, according to another operation 2185, it can be optionally be determined whether or not an improvement criterion is met. The improvement criterion can be of the later paced QRS complex over the earlier paced QRS complex. For instance, the improvement criterion may include that an amplitude of the later QRS complex is larger than that of the earlier QRS complex.

If, at the operation 2185, the answer is no then, execution proceeds to the operation 2191, where it can be determined whether or not a second shock criterion is met. The second shock criterion can optionally be the same as the first shock criterion. Then execution may proceed to operation 2195 as per the above.

If, however, at the operation 2185, the answer is yes, then execution may return to operation 2110 and a false positive may have been avoided. Or, the patient entered into a legitimate crisis enough for the alert at the operation 2135 to be valid, but then simply their situation improved.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

At least one of the methods of this description, when implemented by a processor, can be performed at the rate of at least 10 times per second.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardioverter defibrillator (WCD) system configured for use by a patient with an implanted heart pacing device that is configured to occasionally emit pacing signals, the WCD system comprising:
   an energy storage module configured to store an electrical charge;
   an electrode;
   a support structure configured to be worn by the patient to maintain the electrode on a body of the patient;
   a plurality of sensors that pairwise define a plurality of distinct vectors, each vector of the plurality of distinct vectors having a respective channel, wherein each pair of the plurality of sensors is configured to sense a respective electrocardiogram (ECG) signal portion of the patient along the respective channel;
   a measurement circuit configured to render sets of ECG values, wherein the sets of ECG values include one set corresponding to each of the respective ECG signal portions;
   a pacing signal detection functionality configured to:
      detect sets of pacing artifacts comprising one set of pacing artifacts corresponding to each of the respective ECG signal portions, arising from the occasionally emitted pacing signals that are present in each of the respective ECG signal portions; and
      render sets of pacing values comprising one set of pacing values corresponding to each of the sets of the pacing artifacts; and
   a processor configured to:
      compute a heart rate (HR) value from at least one of the sets of the ECG values;
      determine, from the HR value, whether an alert criterion is met;
      responsive to the alert criterion being met, determine if a preferential channel of the channels has been identified previously;
      attempt inputting at least one of:
         preferential pacing values from the pacing signal detection functionality corresponding to the preferential channel, in response to a successful identification of the preferential channel; and
         generic pacing values from the pacing signal detection functionality corresponding to at least one of the channels, in response to an unsuccessful identification of the preferential channel;
      determine, in view of the attempt to input the preferential pacing values or the generic pacing values, whether a shock criterion is met; and
      responsive to the shock criterion being met, cause at least some of the stored electrical charge to be discharged via the electrode through the patient to deliver a shock to the patient.

2. The WCD system of claim 1, wherein:
the pacing signal detection functionality is implemented at least in part by the measurement circuit.

3. The WCD system of claim 1, wherein:
the pacing signal detection functionality is implemented at least in part by the processor.

4. The WCD system of claim 1, wherein:
the pacing signal detection functionality is implemented at least in part by a pacing detector module distinct from the processor and from the measurement circuit.

5. The WCD system of claim 1, wherein:
the pacing signal detection functionality is configured to detect sets of pacing artifacts included in the respective ECG signal portions by:
filtering the ECG signal portions for detecting possible pacing artifacts;
determining whether or not selected ones of the detected possible pacing artifacts meet a validation criterion; and
confirming, responsive to the validation criterion being met, the selected possible pacing artifacts as the pacing artifacts.

6. The WCD system of claim 5, wherein:
the validation criterion includes that the possible pacing artifacts occur at regular time intervals.

7. The WCD system of claim 1, wherein the processor is further configured to:
compute a value for a status parameter from the HR value, and the alert criterion is met if the computed value for the status parameter exceeds an alert threshold.

8. The WCD system of claim 7, wherein the processor is further configured to:
  identify a QRS complex in the respective ECG signal portions or in the respective sets of ECG values, and
  measure a pulse width of the identified QRS complex, wherein the value for the status parameter is computed from the measured pulse width.

9. The WCD system of claim 1, further comprising:
  a pacer implanted flag configured to have a value of at least true or false, and wherein the processor is further configured to:
  responsive to the pacer implanted flag having a true value, attempt inputting of respective pacing values within the sets of pacing values rendered by the pacing signal detection functionality; and
  responsive to the pacer implanted flag having a false value, determine whether a default shock criterion is met, and wherein:
    responsive to the default shock criterion being met, cause at least some of the stored electrical charge to be discharged via the electrode through the patient to deliver the shock to the patient, and
    responsive to the default shock criterion not being met, prevent discharge of any electrical charge to the patient.

10. The WCD system of claim 1, wherein:
  responsive to the alert criterion being met, the preferential channel not being previously identified, and the attempt to input the generic pacing values corresponding to two of the channels being successful, the processor is further configured to:
  identify one of the two channels as the preferential channel; and
  in response to the identifying, establish the preferential channel.

11. The WCD system of claim 10, wherein the one of the two channels is identified as the preferential channel when a first set of pacing values corresponding to the one of the two channels meet a preference criterion better than a second set of pacing values corresponding to another one of the two channels.

12. The WCD system of claim 11, wherein the preference criterion comprises that pacing artifacts in a first set of pacing artifacts corresponding to the one of the two channels occur within a threshold time difference from pacing artifacts in a second set of pacing artifacts corresponding to the another one of the two channels.

13. The WCD system of claim 1, wherein the processor is further configured to:
  responsive to the alert criterion not being met:
    attempt inputting two sets of generic pacing values rendered by the pacing signal detection functionality corresponding to two candidate channels of the channels; and
    responsive to a successful attempt of inputting the two sets of the generic pacing values:
      determine that a set of the generic pacing values that corresponds to a first one of the two candidate channels meets a preference criterion better than a set of the generic pacing values that corresponds to a second one of the two candidate channels;
      in response to the determining, identifying the first one of the two candidate channels as the preferential channel of the channels; and
      in response to the identifying, establish the preferential channel.

14. The WCD system of claim 13, wherein the attempt to input the two sets of generic pacing values is performed responsive to the preferential channel not being previously identified.

15. The WCD system of claim 13, further comprising:
  a memory, wherein the processor is further configured to establish the preferential channel by storing, in the memory, an indication of the identified first one of the two candidate channels as the preferential channel.

16. The WCD system of claim 13, further comprising:
  an input multiplexer configured to receive the sets of ECG values, wherein the processor is further configured to establish the preferential channel by adjusting the input multiplexer to advance to a next stage a set of the ECG values corresponding to the preferential channel.

17. The WCD system of claim 13, wherein the preference criterion comprises that pacing artifacts corresponding to the first one of the two candidate channels occur within a threshold time difference from pacing artifacts corresponding to the second one of the two candidate channels.

18. The WCD system of claim 1, wherein the processor is further configured to:
  responsive to the successful identification of the preferential channel,
  determine whether the attempt to input the preferential pacing values is successful.

19. The WCD system of claim 18, wherein the processor is further configured to:
  responsive to a determination that the attempt to input the preferential pacing values is successful, determine whether a first shock criterion is met in view of the preferential pacing values; and
  perform at least one of:
    responsive to the first shock criterion being met, cause discharge of at least some of the stored electrical charge via the electrode through the patient to deliver a shock to the patient; and
    responsive to the first shock criterion not being met, prevent discharge of any electrical charge to the patient.

20. The WCD system of claim 18, wherein the processor is further configured to:
  responsive to a determination that the attempt to input the preferential pacing values is unsuccessful, determine whether a second shock criterion is met; and
  perform at least one of:
    responsive to the second shock criterion being met, cause discharge of at least some of the stored electrical charge via the electrode through the patient to deliver a shock to the patient; and
    responsive to the second shock criterion not being met, prevent discharge of any electrical charge to the patient.

21. The WCD system of claim 1, wherein the processor is further configured to:
  responsive to the unsuccessful identification of the preferential channel,
  determine whether the attempt to input the generic pacing values is successful.

22. The WCD system of claim 21, wherein the processor is further configured to:
  responsive to a determination that the attempt to input the generic pacing values is successful, determine whether a third shock criterion is met in view of the generic pacing values; and perform at least one of:
- responsive to the third shock criterion being met, cause discharge of at least some of the stored electrical charge via the electrode through the patient to deliver a shock to the patient; and
- responsive to the third shock criterion not being met, prevent discharge of any electrical charge to the patient.

23. The WCD system of claim 21, wherein the processor is further configured to:
- responsive to a determination that the attempt to input the generic pacing values is unsuccessful, determine whether a fourth shock criterion is met; and
- perform at least one of:
  - responsive to the fourth shock criterion being met, cause discharge of at least some of the stored electrical charge via the electrode through the patient to deliver a shock to the patient; and
  - responsive to the fourth shock criterion not being met, prevent discharge of any electrical charge to the patient.

* * * * *